United States Patent
Ready-Campbell et al.

(10) Patent No.: US 10,982,408 B2
(45) Date of Patent: *Apr. 20, 2021

(54) CHECKING VOLUME IN AN EXCAVATION TOOL

(71) Applicant: Built Robotics Inc., San Francisco, CA (US)

(72) Inventors: Noah Austen Ready-Campbell, San Francisco, CA (US); Andrew Xiao Liang, San Francisco, CA (US); Linus Page Chou, San Francisco, CA (US); Edward Stephen Walker, Jr., San Francisco, CA (US); Christian John Wawrzonek, San Francisco, CA (US); Cyrus Mcmann Ready-Campbell, San Francisco, CA (US)

(73) Assignee: Built Robotics Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/080,753

(22) Filed: Oct. 26, 2020

(65) Prior Publication Data

US 2021/0040706 A1    Feb. 11, 2021

Related U.S. Application Data

(63) Continuation of application No. 16/845,371, filed on Apr. 10, 2020, which is a continuation of application
(Continued)

(51) Int. Cl.
*E02F 9/16* (2006.01)
*E02F 3/43* (2006.01)
(Continued)

(52) U.S. Cl.
CPC ............... *E02F 3/435* (2013.01); *E02F 3/32* (2013.01); *E02F 3/434* (2013.01); *E02F 3/439* (2013.01);
(Continued)

(58) Field of Classification Search
CPC . E02F 3/435; E02F 3/964; E02F 9/205; E02F 9/2029; E02F 3/439; E02F 3/434; E02F 9/265; E02F 3/32; E02F 9/262
See application file for complete search history.

(56) References Cited

U.S. PATENT DOCUMENTS 5,768,810 A    6/1998  Ahn
5,974,352 A    10/1999 Shul
(Continued)

FOREIGN PATENT DOCUMENTS

AU    2016200782 B1    5/2016
CN    105960492 A      9/2016

OTHER PUBLICATIONS

International Search Report and Written Opinion, PCT Patent Application No. PCT/US2018/014727, dated May 16, 2018, 21 pages.
(Continued)

*Primary Examiner* — Edwin J Toledo-Duran
(74) *Attorney, Agent, or Firm* — Fenwick & West LLP

(57) ABSTRACT

This description provides an autonomous or semi-autonomous excavation vehicle that is capable of navigating through a dig site and carrying out an excavation routine using a system of sensors physically mounted to the excavation vehicle. The sensors collects any one or more of spatial, imaging, measurement, and location data representing the status of the excavation vehicle and its surrounding environment. Based on the collected data, the excavation vehicle executes instructions to carry out an excavation
(Continued)

routine. The excavation vehicle is also able to carry out numerous other tasks, such as checking the volume of excavated earth in an excavation tool, and helping prepare a digital terrain model of the site as part of a process for creating the excavation routine.

23 Claims, 15 Drawing Sheets

Related U.S. Application Data

No. 15/877,223, filed on Jan. 22, 2018, now Pat. No. 10,662,613.

(60) Provisional application No. 62/449,443, filed on Jan. 23, 2017, provisional application No. 62/510,576, filed on May 24, 2017, provisional application No. 62/514,341, filed on Jun. 2, 2017.

(51) Int. Cl.
  E02F 9/26 (2006.01)
  E02F 3/32 (2006.01)
  E02F 9/20 (2006.01)
  E02F 3/96 (2006.01)

(52) U.S. Cl.
  CPC ............ *E02F 3/964* (2013.01); *E02F 9/205* (2013.01); *E02F 9/2029* (2013.01); *E02F 9/262* (2013.01); *E02F 9/265* (2013.01)

(56) References Cited

U.S. PATENT DOCUMENTS

| | | | |
|---|---|---|---|
| 6,108,949 A | 8/2000 | Singh et al. | |
| 6,167,336 A | 12/2000 | Singh et al. | |
| 6,363,632 B1 | 4/2002 | Stentz et al. | |
| 6,823,616 B1 | 11/2004 | Gutter et al. | |
| 7,627,410 B2 | 12/2009 | Berry et al. | |
| 7,853,382 B2 | 12/2010 | Anderson | |
| 8,160,783 B2 | 4/2012 | Shull | |
| 8,363,210 B2 | 1/2013 | Montgomery | |
| 8,364,353 B2 | 1/2013 | Kiegerl et al. | |
| 8,654,608 B2 | 2/2014 | Lindskov | |
| 8,726,647 B2 | 5/2014 | Peterson et al. | |
| 8,768,579 B2 | 7/2014 | Taylor et al. | |
| 8,838,331 B2 | 9/2014 | Jensen | |
| 8,903,689 B2 | 12/2014 | Dunbabin et al. | |
| 9,206,587 B2 | 12/2015 | Linstroth et al. | |
| 9,228,321 B1 | 1/2016 | Stratton et al. | |
| 9,256,227 B1 | 2/2016 | Wei et al. | |
| 9,297,147 B1 | 3/2016 | Wei et al. | |
| 9,360,334 B2 | 6/2016 | Wei et al. | |
| 9,404,239 B2 | 8/2016 | Wei et al. | |
| 9,458,598 B2 | 10/2016 | Takaura et al. | |
| 9,469,967 B2 | 10/2016 | Edara et al. | |
| 9,481,977 B1 | 11/2016 | Clar et al. | |
| 9,605,415 B2 | 3/2017 | Edara et al. | |
| 9,760,081 B2 | 9/2017 | Taylor et al. | |
| 10,066,367 B1 | 9/2018 | Wang et al. | |
| 10,101,723 B2 | 10/2018 | Wei et al. | |
| 10,146,220 B2 | 12/2018 | McHugh et al. | |
| 10,151,078 B1 | 12/2018 | Metzger et al. | |
| 10,208,453 B2 | 2/2019 | Taylor et al. | |
| 10,267,018 B2 | 4/2019 | Benson et al. | |
| 10,407,878 B2 | 9/2019 | Wei | |
| 10,472,803 B2 | 11/2019 | Wei | |
| 10,774,506 B2 | 9/2020 | Wei | |
| 10,794,039 B2 | 10/2020 | Wei et al. | |
| 10,832,435 B1 | 11/2020 | Mathew et al. | |
| 2003/0019132 A1 | 1/2003 | Kurenuma et al. | |
| 2003/0115779 A1 | 6/2003 | Satzler et al. | |
| 2004/0020083 A1 | 2/2004 | Staub et al. | |
| 2007/0219720 A1 | 9/2007 | Trepagnier | |
| 2007/0240341 A1 | 10/2007 | Hyde | |
| 2007/0260380 A1 | 11/2007 | Mintah et al. | |
| 2007/0299590 A1 | 12/2007 | Shull et al. | |
| 2008/0133128 A1 | 6/2008 | Koch | |
| 2008/0162004 A1 | 7/2008 | Price et al. | |
| 2008/0282583 A1 | 11/2008 | Koellner et al. | |
| 2010/0223008 A1 | 9/2010 | Dunbabin et al. | |
| 2012/0046822 A1 | 2/2012 | Anderson | |
| 2012/0136508 A1 | 5/2012 | Taylor et al. | |
| 2012/0215378 A1 | 8/2012 | Sprock et al. | |
| 2013/0006484 A1 | 1/2013 | Avitzur et al. | |
| 2013/0311031 A1 | 11/2013 | Friend et al. | |
| 2014/0012404 A1 | 1/2014 | Taylor et al. | |
| 2014/0032132 A1 | 1/2014 | Stratton et al. | |
| 2014/0064897 A1 | 3/2014 | Montgomery | |
| 2014/0088838 A1 | 3/2014 | Furem et al. | |
| 2014/0174770 A1 | 6/2014 | Wei et al. | |
| 2014/0180548 A1 | 6/2014 | Edara et al. | |
| 2014/0277957 A1 | 9/2014 | Clar et al. | |
| 2015/0050110 A1 | 2/2015 | Matsuyama et al. | |
| 2015/0276468 A1 | 10/2015 | Jaeger | |
| 2016/0040392 A1 | 2/2016 | Kontz | |
| 2016/0076222 A1 | 3/2016 | Taylor et al. | |
| 2016/0076223 A1 | 3/2016 | Wei et al. | |
| 2016/0194850 A1 | 7/2016 | Taylor et al. | |
| 2016/0201298 A1 | 7/2016 | Taylor et al. | |
| 2016/0312434 A1 | 10/2016 | Shintani et al. | |
| 2016/0312446 A1 | 10/2016 | Petterson et al. | |
| 2016/0343095 A1 | 11/2016 | Wei et al. | |
| 2017/0002540 A1* | 1/2017 | Fletcher | E02F 9/205 |
| 2017/0073935 A1 | 3/2017 | Friend et al. | |
| 2017/0138017 A1 | 5/2017 | Halepatali et al. | |
| 2017/0247860 A1 | 8/2017 | Lehtinen et al. | |
| 2017/0255895 A1 | 9/2017 | Kozumi et al. | |
| 2018/0038068 A1 | 2/2018 | Hashimoto et al. | |
| 2018/0038069 A1 | 2/2018 | Hashimoto et al. | |
| 2018/0038070 A1 | 2/2018 | Hashimoto et al. | |
| 2018/0038082 A1 | 2/2018 | Hashimoto et al. | |
| 2018/0044888 A1* | 2/2018 | Chi | G06F 3/0484 |
| 2018/0106709 A1 | 4/2018 | Cherney | |
| 2018/0179737 A1 | 6/2018 | Friend et al. | |
| 2018/0210454 A1 | 7/2018 | Ready-Campbell et al. | |
| 2018/0230673 A1 | 8/2018 | Lee et al. | |
| 2018/0245317 A1 | 8/2018 | Ready-Campbell et al. | |
| 2018/0319392 A1 | 11/2018 | Posselius et al. | |
| 2019/0101641 A1 | 4/2019 | Hogan et al. | |
| 2019/0217857 A1 | 7/2019 | Sorin et al. | |
| 2019/0218745 A1 | 7/2019 | Hashimoto | |
| 2019/0226175 A1 | 7/2019 | Mairet et al. | |
| 2020/0019192 A1 | 1/2020 | O'Donnell | |
| 2020/0032483 A1 | 1/2020 | Ready-Campbell et al. | |
| 2020/0032490 A1 | 1/2020 | Ready-Campbell et al. | |
| 2020/0040555 A1 | 2/2020 | Hageman et al. | |
| 2020/0041331 A1 | 2/2020 | Hoshino et al. | |
| 2020/0063395 A1 | 2/2020 | Ready-Campbell et al. | |
| 2020/0087893 A1 | 3/2020 | Hageman et al. | |

OTHER PUBLICATIONS

Examination report No. 1, IP Australia Patent Application No. 2018210524, dated Aug. 14, 2020, 10 pages.
United States Office Action, U.S. Appl. No. 15/877,221, dated Oct. 13, 2020, 21 pages.
United States Office Action, U.S. Appl. No. 15/877,221, dated Apr. 23, 2020, 29 pages.
European Patent Office, Extended European Search Report and Opinion, EP Patent Application No. 18742299.3, dated Nov. 4, 2020, eight pages.
United States Office Action, U.S. Appl. No. 17/066,480, dated Dec. 9, 2020, 16 pages.
United States Office Action, U.S. Appl. No. 17/066,481, dated Dec. 10, 2020, 14 pages.

* cited by examiner

CHECKING VOLUME IN AN EXCAVATION TOOL

CROSS REFERENCE TO RELATED APPLICATIONS

This application is a continuation of U.S. patent Ser. No. 16/845,371, filed Apr. 10, 2020, which is a continuation of U.S. patent Ser. No. 15/877,223, filed on Jan. 22, 2018, now U.S. Pat. No. 10,662,613, issued on May 26, 2020, which claims benefit of U.S. Provisional Patent Application No. 62/449,443 filed on Jan. 23, 2017; 62/510,576, filed on May 24, 2017; and 62/514,341, filed Jun. 2, 2017, all of which are herein incorporated in their entirety for all purposes.

BACKGROUND

Field of Art

The disclosure relates generally to method for excavating earth from a dig site, and more specifically to excavating earth using a vehicle operated using a sensor assembly coupled to control the vehicle.

Description of the Related Art

Vehicles such as backhoes, loaders, and excavators, generally categorized as excavation vehicles, are used to excavate earth from locations. Currently, operation of these excavation vehicles is very expensive as each vehicle requires a manual operator be available and present during the entire excavation. Further complicating the field, there is an insufficient labor force skilled enough to meet the demand for operating these vehicles. Because they must be operated manually, excavation can only be performed during the day, extending the duration of excavation projects and further increasing overall costs. The dependence of current excavation vehicles on manual operators increases the risk of human error during excavations and reduce the quality of work done at the site.

SUMMARY

Described is an autonomous or semi-autonomous excavation system that unifies an excavation vehicle with a sensor system for excavating earth from a site. The excavation system controls and navigates an excavation vehicle through an excavation routine of a site. The excavation system uses a combination of sensors integrated into the excavation vehicle to record the positions and orientations of the various components of the excavation vehicle and/or the conditions of the surrounding earth. Data recorded by the sensors may be aggregated or processed in various ways, for example, to determine and control the actuation of the vehicle's controls, to generate representations of the current state of the site, to perform measurements and generate analyses based on those measurements, and perform other tasks described herein.

According to an embodiment, a method for preparing a representation of a site includes receiving a digital file of the site describing a planned hole yet to be excavated and an area surrounding the planned hole. In the digital file, the site is represented as a coordinate space with respect to a geographic map. The excavation vehicle navigates the site and concurrently records contextual information about the site with a sensor physically mounted on the excavation vehicle. The sensor records contextual information, at different positions and orientations, as representations of a current physical state of the site. The method also includes using the received digital file and the recorded contextual information to generate a digital terrain model of the site. The digital terrain model includes a volume of earth to be excavated to form the planned hole. Using the digital terrain model, the method includes generating a plurality of target tool paths to be carried out by a tool mounted to the excavation vehicle for the excavation of the volume of earth from the site.

According to an embodiment, a method for removing a volume of earth from a site includes accessing a plurality of target tool paths from a coupled computer memory. The target tool paths describe a set of coordinates within a coordinate space of the site and represent a portion of the volume of earth to be removed. The method also includes executing, with a computer coupled to the excavation vehicle, a set of instructions for excavating the volume of earth. To execute the instructions, the excavation vehicle positions the leading edge of a tool of the excavation vehicle at depth below the surface of the earth, moving the tool a first distance along the target tool path, and measuring the tool. The excavation vehicle also determines that the fill level is below a threshold and moves the tool a second distance along the target tool path.

According to an embodiment, a method for analyzing an amount of earth in a tool includes recording data representing a current fill state of a tool mounted to the excavation vehicle with a sensor and, based on the recorded data, generating, by a coupled computer, a current representation of the amount of earth in the tool. The method also includes accessing, from a computer memory coupled to the excavation vehicle, an empty representation of the tool and, based on a different between the current representation and the empty representation, determining a volume of earth within the tool. In response to the volume of earth being less than a threshold, the method includes executing, by the coupled computer, a set of instructions to set a leading edge of the tool below a ground surface to continue or repeat a target tool path.

The described excavation system reduces the cost of excavating a site by reducing the need for manual labor, by obtaining actionable information that helps design and increase the efficiency of the excavation project, and by improving the overall quality and precision of the project by carrying out consistent, repeatable actions in accordance with excavation plans.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. Excavation System

Figure 1:
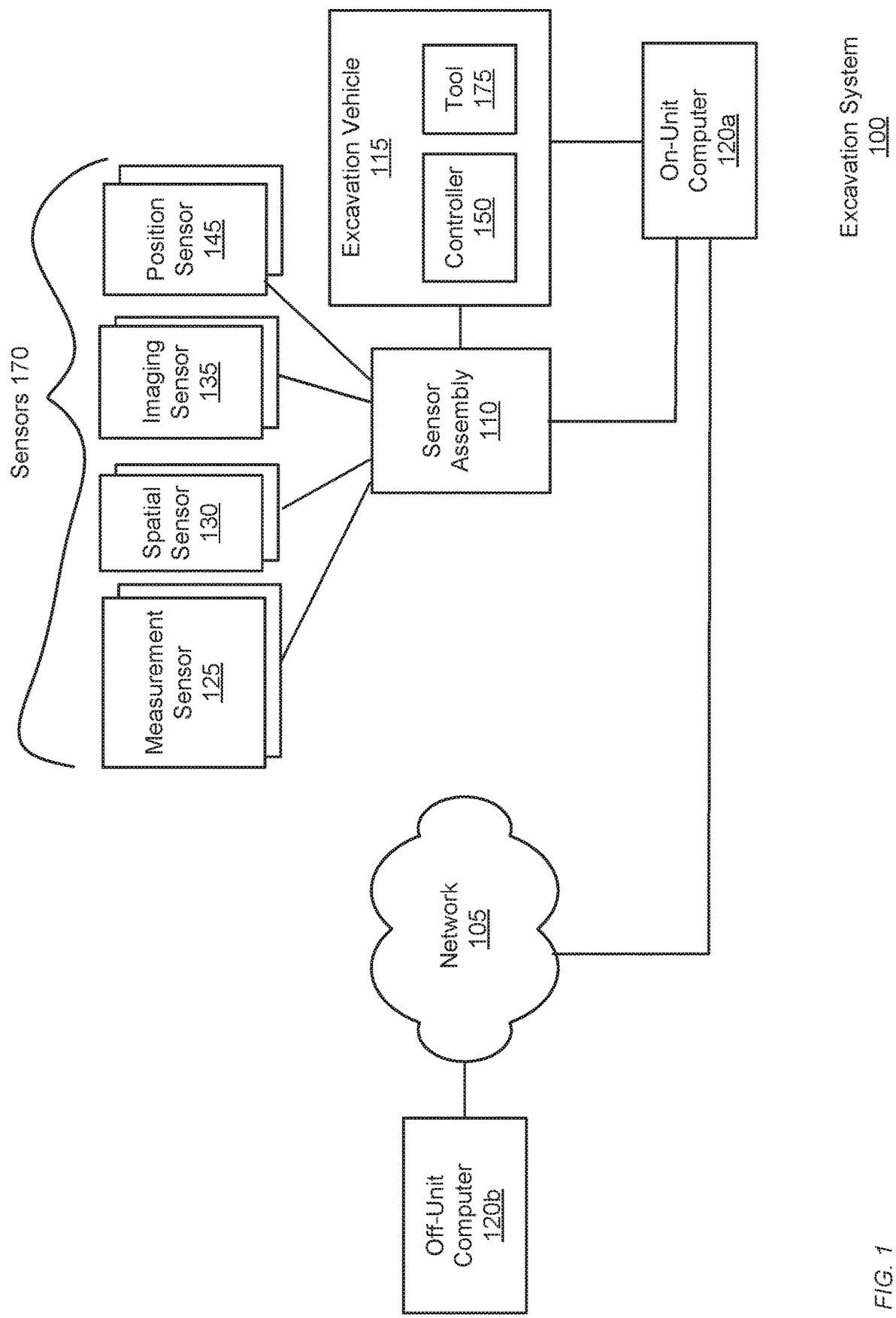
FIG. 1 shows an excavation system for excavating earth, according to an embodiment.
Figure 2A:
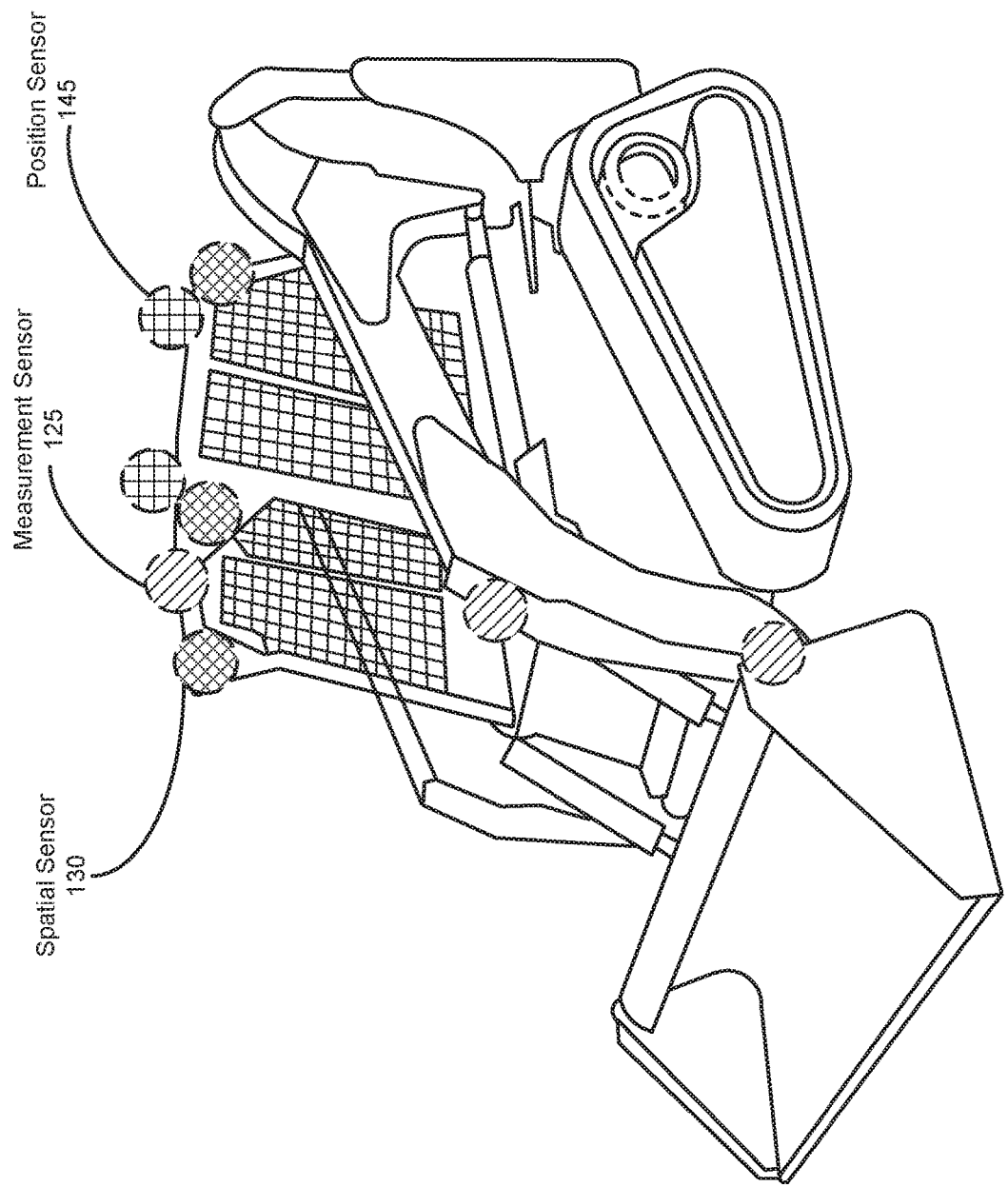
FIG. 2A illustrates the example placement of sensors for a compact track loader, according to an embodiment.
Figure 2B:
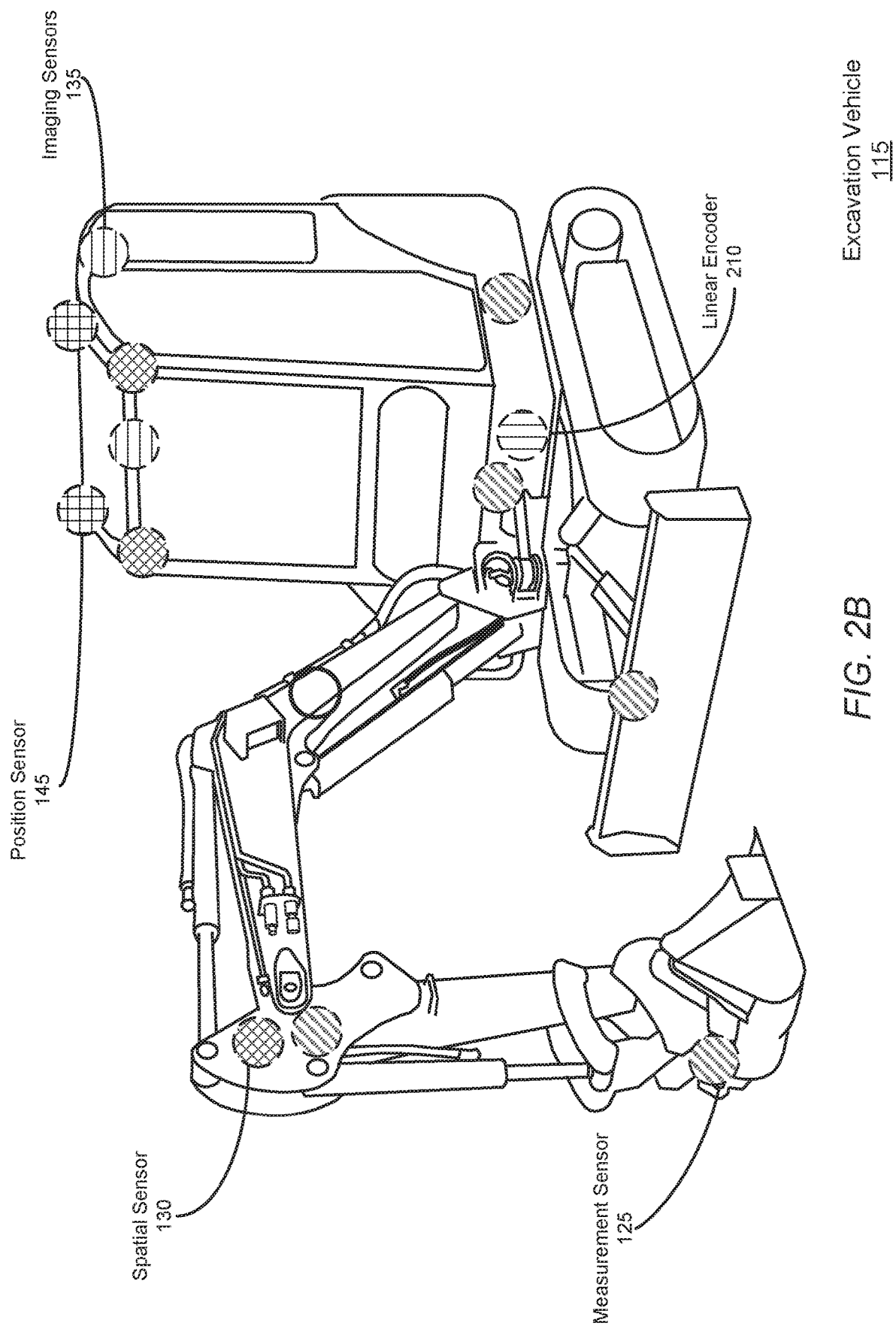
FIG. 2B illustrates the example placement of sensors for an excavator, according to an embodiment.

FIG. 1 shows an excavation system 100 for excavating earth autonomously or semi-autonomously from a dig site using a suite of one or more sensors 170 mounted on an excavation vehicle 115 to record data describing the state of the excavation vehicle 115 and the excavated site. As examples, FIGS. 2A and 2B illustrate the example placement of sensors for a compact track loader and an excavator, respectively, according to example embodiments. FIGS. 1-2B are discussed together in the following section for clarity.

The excavation system 100 includes a set of components physically coupled to the excavation vehicle 115. These include a sensor assembly 110, the excavation vehicle 115 itself, a digital or analog electrical controller 150, and an on-unit computer 120a. The sensor assembly no includes one or more of any of the following types of sensors: measurement sensors 125, spatial sensors 130, imaging sensors 135, and position sensors 145.

Each of these components will be discussed further below in the remaining sub-sections of FIG. 1. Although FIG. 1 illustrates only a single instance of most of the components of the excavation system 100, in practice more than one of each component may be present, and additional or fewer components may be used different than those described herein.

I.A. Excavation Vehicle

The excavation vehicle 115 is an item of heavy equipment designed to excavate earth from a hole within a dig site. Excavation vehicles 115 are typically large and capable of moving large volumes of earth at a single time, particularly relative to what an individual human can move by hand. Generally, excavation vehicles 115 excavate earth by scraping or digging earth from beneath the ground surface. Examples of excavation vehicles 115 within the scope of this description include, but are not limited to loaders such as backhoe loaders, track loaders, wheel loaders, skid steer loaders, scrapers, graders, bulldozers, compactors, excavators, mini-excavators, trenchers, skip loaders.

Among other components, excavation vehicles 115 generally include a chassis 205, a drive system 210, an excavation tool 175, an engine (not shown), an on-board sensor assembly 110, and a controller 150. The chassis 205 is the frame upon on which all other components are physically mounted. The drive system 210 210 give the excavation vehicle 115 mobility through the excavation site. The excavation tool 175 includes not only the instrument collecting dirt, such as a bucket or shovel, but also any articulated elements for positioning the instrument for the collection, measurement, and dumping of dirt. For example, in an excavator or loader the excavation tool refers not only the bucket but also the multi-element arm that adjusts the position and orientation of the tool.

The engine powers both the drive system 210 and the excavation tool 175. The engine may be an internal combustion engine, or an alternative power plant, such as an electric motor or battery. In many excavation vehicles 115, the engine powers the drive system 210 and the excavation tool commonly through a single hydraulic system, however other means of actuation may also be used. A common property of hydraulic systems used within excavation vehicles 115 is that the hydraulic capacity of the vehicle 115 is shared between the drive system 210 and the excavation tool. In some embodiments, the instructions and control logic for the excavation vehicle 115 to operate autonomously and semi-autonomously includes instructions relating to determinations about how and under what circumstances to allocate the hydraulic capacity of the hydraulic system.

I.B. Sensor Assembly

As introduced above, the sensor assembly no includes a combination of one or more of: measurement sensors 125, spatial sensors 130, imaging sensors 135, and position sensors 145. The sensor assembly no is configured to collect data related to the excavation vehicle 115 and environmental data surrounding the excavation vehicle 115. The controller 150 is configured to receive the data from the assembly no and carry out the instructions of the excavation routine provided by the computers 120 based on the recorded data. This includes control the drive system 210 to move the position of the tool based on the environmental data, a location of the excavation vehicle 115, and the excavation routine.

Sensors 170 are either removably mounted to the excavation vehicle 115 without impeding the operation of the excavation vehicle 115, or the sensor is an integrated component that is a native part of the excavation vehicle 115 as made available by its manufacturer. Each sensor transmits the data in real-time or as soon as a network connection is achieved, automatically without input from the excavation vehicle 115 or a human operator. Data recorded by the sensors 170 is used by the controller 150 and/or on-unit computer 120a for analysis of, generation of and carrying out of excavation routines, among other tasks.

Position sensors 145 provide a position of the excavation vehicle 115. This may be a localized position within a dig site, or a global position with respect latitude/longitude, or some other external reference system. In one embodiment, a position sensor is a global positioning system interfacing with a static local ground-based GPS node mounted to the excavation vehicle 115 to output a position of the excavation vehicle 115.

Spatial sensors 130 output a three-dimensional map in the form of a three-dimensional point cloud representing distances between one meter and fifty meters between the spatial sensors 130 and the ground surface or any objects within the field of view of the spatial sensor 130, in some cases per rotation of the spatial sensor 130. In one embodiment, spatial sensors 130 include a set of light emitters (e.g., Infrared (IR)) configured to project structured light into a field near the excavation vehicle 115, a set of detectors (e.g., IR cameras), and a processor configured to transform data received by the infrared detectors into a point cloud representation of the three-dimensional volume captured by the detectors as measured by structured light reflected by the environment. In one embodiment, the spatial sensor 130 is a LIDAR sensor having a scan cycle that sweeps through an angular range capturing some or all of the volume of space surrounding the excavation vehicle 115. Other types of spatial sensors 130 may be used, including time-of-flight sensors, ultrasonic sensors, and radar sensors.

Imaging sensors 135 capture still or moving-video representations of the ground surface, objects, and environment surrounding the excavation vehicle 115. Examples imaging sensors 135 include, but are not limited to, stereo RGB cameras, structure from motion cameras, and monocular RGB cameras. In one embodiment, each camera can output a video feed containing a sequence of digital photographic images at a rate of 20 Hz. In one embodiment, multiple imaging sensors 135 are mounted such that each imaging sensor captures some portion of the entire 360 degree angular range around the vehicle. For example, front, rear, left lateral, and right lateral imaging sensors may be mounted to capture the entire angular range around the excavation vehicle 115.

Measurement sensors 125 generally measure properties of the ambient environment, or properties of the excavation vehicle 115 itself. These properties may include tool position/orientation, relative articulation of the various joints of the arm supporting the tool, vehicle 115 speed, ambient temperature, hydraulic pressure (either relative to capacity or absolute) including how much hydraulic capacity is being used by the drive system 210 and the excavation tool separately. A variety of possible measurement sensors 125 may be used, including hydraulic pressure sensors, linear encoders, radial encoders, inertial measurement unit sensors, incline sensors, accelerometers, strain gauges, gyroscopes, and string encoders.

There are a number of different ways for the sensor assembly no generally and the individual sensors specifically to be constructed and/or mounted to the excavation vehicle 115. This will also depend in part on the construction of the excavation vehicle 115. Using the compact track loader of FIG. 2A as an example, the representations with diagonal crosshatching represent the example placements of a set of measurement sensors 125, the representation with diamond crosshatching represent example placements of a set of spatial sensors 130, and the representations with grid crosshatching represent example placements of a set of position sensors 145. Using the excavator of FIG. 2B as another example, diagonal crosshatchings represent measurement sensors 125, diamond crosshatchings represent spatial sensors 130, and grid crosshatchings represent position sensors 145. Additionally vertical crosshatchings near the drive system 210 represent example placements for a linear encoder 210 and horizontal crosshatchings near the roof represent imaging sensors 135, for example RGB cameras.

Generally, individual sensors as well as the sensor assembly 110 itself range in complexity from simplistic measurement devices that output analog or electrical systems electrically coupled to a network bus or other communicative network, to more complicated devices which include their own onboard computer processors, memory, and the communications adapters (similar to on-unit computer 120a). Regardless of construction, the sensors and/or sensor assembly together function to record, store, and report information to the computers 120. Any given sensor may record or the sensor assembly may append to recorded data a time stamps for when data was recorded.

The sensor assembly 110 may include its own network adapter (not shown) that communicates with the computers 120 either through either a wired or wireless connection. For wireless connections, the network adapter may be a Bluetooth Low Energy (BTLE) wireless transmitter, infrared, or 802.11 based connection. For wired connection, a wide variety of communications standards and related architecture may be used, including Ethernet, a Controller Area Network (CAN) Bus, or similar.

In the case of a BTLE connection, After the sensor assembly 110 and on-unit computer 120a have been paired with each other using a BLTE passkey, the sensor assembly 110 automatically synchronizes and communicates information relating to the excavation of a site to the on-site computer 120a. If the sensor assembly 110 has not been paired with the on-unit computer 120 prior to the excavation of a site, the information is stored locally until such a pairing occurs. Upon pairing, the sensor assembly 110 communicates any stored data to the on-site computer 120a.

The sensor assembly 110 may be configured to communicate received data to any one of the controller 150 of the excavation vehicle 115, the on-unit computer 120a, as well as the off-unit computer 120b. For example, if the network adapter of the sensor assembly no is configured to communicate via a wireless standard such as 802.11 or LTE, the adapter may exchange data with a wireless access point such as a wireless router, which may in turn communicate with the off-unit computer 120b and also on-unit computer 120a. This type of transmission may be redundant, but it can help ensure that recorded data arrives at the off-unit computer 120b for consumption and decision making by a manual operator, while also providing the data to the on-unit computer 120a for autonomous or semi-autonomous decision making in the carrying out of the excavation plan.

I.C. On-Unit Computer

Data collected by the sensors 170 is communicated to the on-unit computer 120a to assist in the design or carrying out of an excavation routine. Generally, excavation routines are sets of computer program instructions that, when executed control the various controllable inputs of the excavation vehicle 115 to carry out an excavation-related task. The controllable input of the excavation vehicle 115 may include the joystick controlling the drive system 210 and excavation tool and any directly-controllable articulable elements, or some controller 150 associated input to those controllable elements, such as an analog or electrical circuit that responds to joystick inputs.

Generally, excavation-related tasks and excavation routines are broadly defined to include any task that can be feasibly carried out by an excavation routine. Examples include, but are not limited to: dig site preparation routines, digging routines, fill estimate routines, volume check routines, dump routines, wall cutback routines, backfill/compaction routines. Examples of these routines are described further below. In addition to instructions, excavation routines include data characterizing the site and the amount and locations of earth to be excavated. Examples of such data include, but are not limited to, a digital file, sensor data, a digital terrain model, and one or more target tool paths. Examples of such data are further described below.

The excavation vehicle 115 is designed to carry out the set of instructions of an excavation routine either entirely autonomously or semi-autonomously. Here, semi-autonomous refers to an excavation vehicle 115 that not only responds to the instructions but also to a manual operator. Manual operators of the excavation vehicle 115 may be monitor the excavation routine from inside of the excavation vehicle using the on-unit computer 120a or remotely using an off-unit computer 120b from outside of the excavation vehicle, on-site, or off-site. Manual operation may take the form of manual input to the joystick, for example. Sensor data is received by the on-unit computer 120a and assists in the carrying out of those instructions, for example by modifying exactly what inputs are provided to the controller 150 in order to achieve the instructions to be accomplished as part of the excavation routine.

The on-unit computer 120a may also exchange information with the off-unit computer 120b and/or other excavation vehicles (not shown) connected through network 105. For example, an excavation vehicle 115 may communicate data recorded by one excavation vehicle 115 to a fleet of additional excavation vehicle 115s that may be used at the same site. Similarly, through the network 105, the computers 120 may deliver data regarding a specific site to a central location from which the fleet of excavation vehicle 115s are stored. This may involve the excavation vehicle 115 exchanging data with the off-unit computer, which in turn can initiate a process to generate the set of instructions for excavating the earth and to deliver the instructions to another excavation vehicle 115. Similarly, the excavation vehicle 115 may also receive data sent by other sensor assemblies no of other excavation vehicles 115 as communicated between computers 120 over network 105.

The on-unit computer 120a may also process the data received from the sensor assembly no. Processing generally takes sensor data that in a "raw" format may not be directly usable, and converts into a form that useful for another type of processing. For example, the on unit computer 120a may fuse data from the various sensors into a real-time scan of the ground surface of the site around the excavation vehicle 115. This may comprise fusing the point clouds of various spatial sensors 130, the stitching of images from multiple imaging sensors 135, and the registration of images and point clouds relative to each other or relative to data regarding an external reference frame as provided by position sensors 145 or other data. Processing may also include up sampling, down sampling, interpolation, filtering, smoothing, or other related techniques.

I.D. Off-Unit Computer

The off-unit computer 120b includes a software architecture for supporting access and use of the excavation system 100 by many different excavation vehicles 115 through network 105, and thus at a high level can be generally characterized as a cloud-based system. Any operations or processing performed by the on-unit computer 120a may also be performed similarly by the off-unit computer 120b.

In some instances, the operation of the excavation vehicle 115 is monitored by a human operator. Human operators, when necessary, may halt or override the automated excavation process and manually operate the excavation vehicle 115 in response to observations made regarding the features or the properties of the site. Monitoring by a human operator may include remote oversight of the whole excavation routine or a portion of it. Human operation of the excavation vehicle 115 may also include manual control of the joysticks of the excavation vehicle 115 for portions of the excavation routine (i.e., preparation routine, digging routine, etc.). Additionally, when appropriate, human operators may override all or a part of the set of instructions and/or excavation routine carried out by the on-unit computer 120a.

I.E. General Computer Structure

The on-unit 120a and off-unit 120b computers may be generic or special purpose computers. A simplified example of the components of an example computer according to one embodiment is illustrated in FIG. 3.

Figure 3:
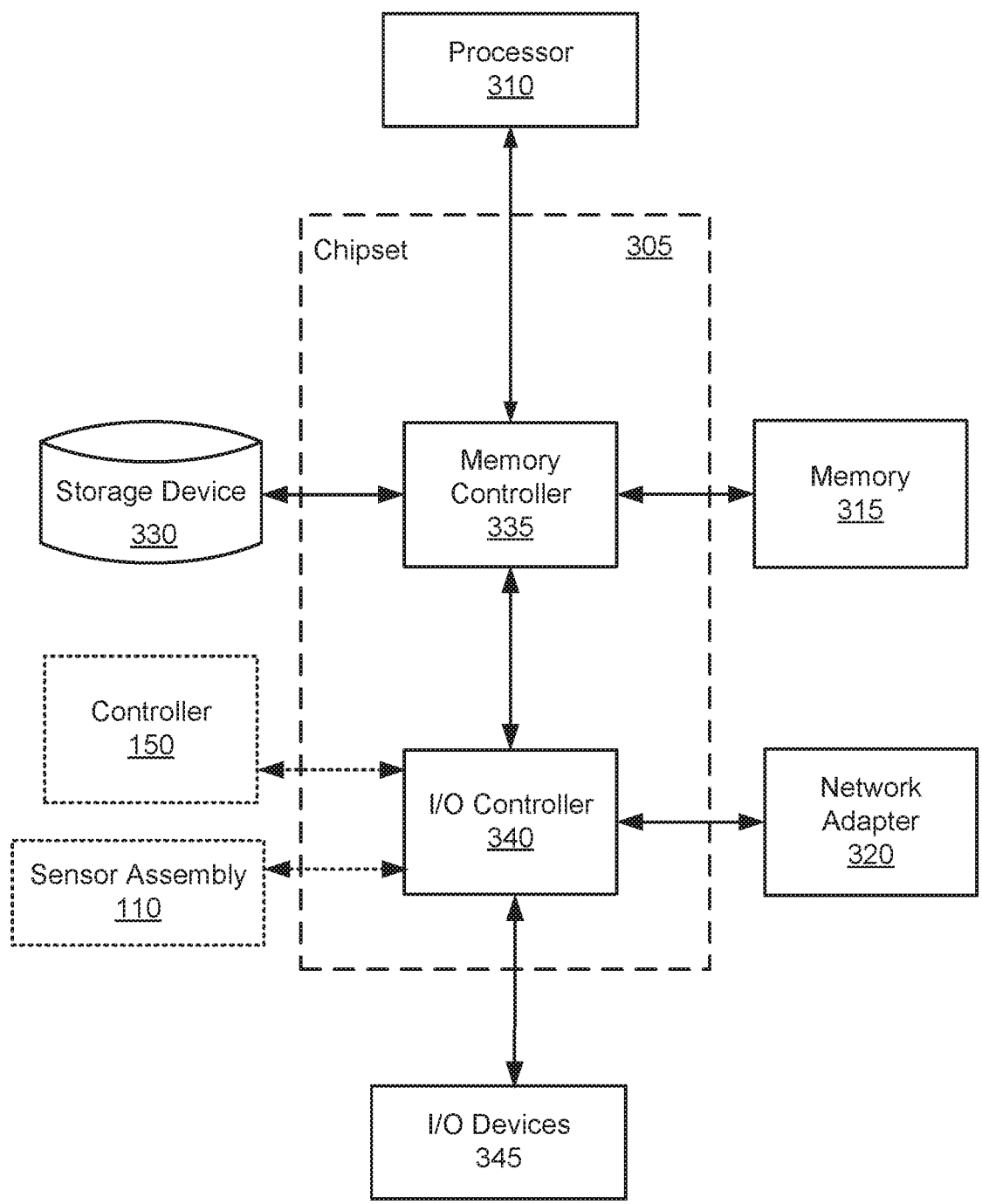
FIG. 3 is a high-level block diagram illustrating an example of a computing device used in an on-unit computer, off-unit computer, and/or database server, according to an embodiment.

FIG. 3 is a high-level block diagram illustrating physical components of an example off-unit computer 120b from FIG. 1, according to one embodiment. Illustrated is a chipset 305 coupled to at least one processor 310. Coupled to the chipset 305 is volatile memory 315, a network adapter 320, an input/output (I/O) device(s) 325, and a storage device 330 representing a non-volatile memory. In one implementation, the functionality of the chipset 305 is provided by a memory controller 335 and an I/O controller 340. In another embodiment, the memory 315 is coupled directly to the processor 310 instead of the chipset 305. In some embodiments, memory 315 includes high-speed random access memory (RAM), such as DRAM, SRAM, DDR RAM or other random access solid state memory devices.

The storage device 330 is any non-transitory computer-readable storage medium, such as a hard drive, compact disk read-only memory (CD-ROM), DVD, or a solid-state memory device. The memory 315 holds instructions and data used by the processor 310. The I/O controller 340 is coupled to receive input from the machine controller 150 and the sensor assembly 110, as described in FIG. 1, and displays data using the I/O devices 345. The I/O device 345 may be a touch input surface (capacitive or otherwise), a mouse, track ball, or other type of pointing device, a keyboard, or another form of input device. The network adapter 320 couples the off-unit computer 120b to the network 105.

As is known in the art, a computer 120 can have different and/or other components than those shown in FIG. 2. In addition, the computer 120 can lack certain illustrated components. In one embodiment, a computer 120 acting as server may lack a dedicated I/O device 345. Moreover, the storage device 330 can be local and/or remote from the computer 120 (such as embodied within a storage area network (SAN)), and, in one embodiment, the storage device 330 is not a CD-ROM device or a DVD device.

Generally, the exact physical components used in the on-unit 120a and off-unit 120b computers will vary. For example, the on-unit computer 120a will be communicatively coupled to the controller 150 and sensor assembly 110 differently than the off-unit computer 120b.

Typically the off-unit computer 120b will be a server class system that uses powerful processors, large memory, and faster network components compared to the on-unit computer 120a, however this is not necessarily the case. Such a server computer typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the off-unit computer 120*b* and also provides various services, for example, process management, input/output of data, management of peripheral devices, and so on. The operating system provides various functions for managing files stored on a device, for example, creating a new file, moving or copying files, transferring files to a remote system, and so on.

As is known in the art, the computer 120 is adapted to execute computer program modules for providing functionality described herein. A module can be implemented in hardware, firmware, and/or software. In one embodiment, program modules are stored on the storage device 330, loaded into the memory 315, and executed by the processor 310.

I.F. Network

The network 105 represents the various wired and wireless communication pathways between the computers 120, the sensor assembly no, and the excavation vehicle 115. Network 105 uses standard Internet communications technologies and/or protocols. Thus, the network 105 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 105F can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Site and Routine Overview

Figure 4:
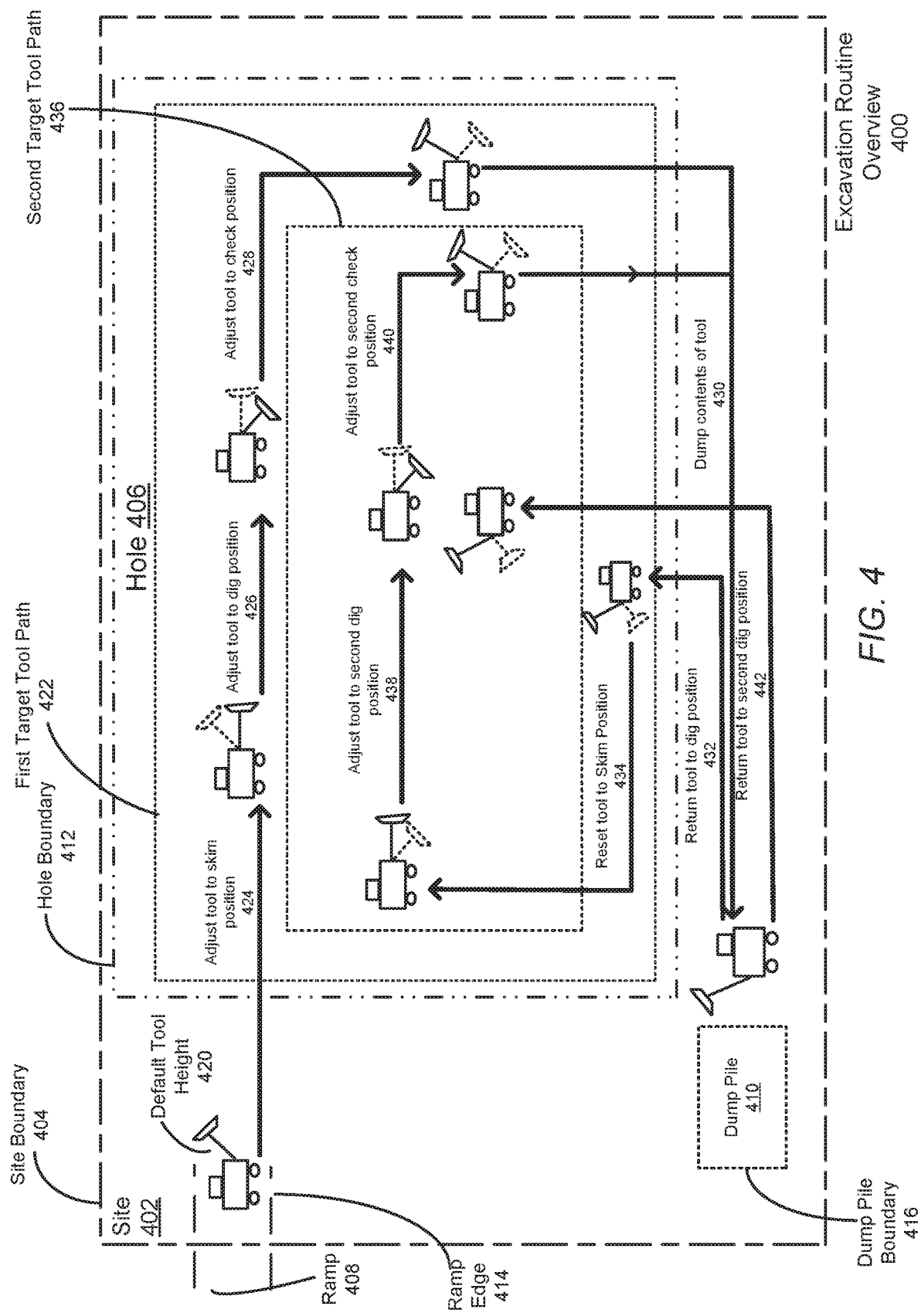
FIG. 4 illustrates an example coordinate space in which an excavation vehicle carries out an excavation routine in a dig site, according to an embodiment.

FIG. 4 illustrates an example coordinate space in which an excavation vehicle carries out an excavation routine in a dig site 402, according to an embodiment. FIG. 4 may be a visual representation of the coordinate space from a digital file detailing the excavation routine. In this example, the excavation routine includes a planned excavation of a hole and the area surrounding the hole. In the digital file, the site 402 is represented as bounded by the site boundary 404. The digital file further includes data describing the location of a hole 406, a ramp 408, and a dump pile 410. The hole 406, bounded by the hole boundary 412, refers to a location within the site where the excavation vehicle 115 within the site where the excavation vehicle 115 will perform the excavation routine described by the set of instructions. The ramp 408 refers to a graded pathway over which the excavation vehicle 115 may traverse to enter/exit the hole 406. In some implementations, a ramp 408 may also be implemented at the site boundary for the excavation vehicle 115 to enter the site 406. The boundaries of the ramp 408 are represented as ramp edges 414. Similar to the hole 406, the dump pile 410, bounded by the dump pile boundary 416, refers to a location within the site where the excavation vehicle 115 releases excavated earth held in the tool. As described herein, earth refers to the ground material and composition of a site, for example, soil, dirt, and gravel.

Walking through an example hypothetical excavation routine for purpose of discussing the concepts introduced in FIG. 4, in one such routine the excavation vehicle 115 travels over the ramp 408 to enter the site 402 or the hole 406. Once in the hole 406, the excavation vehicle 115 executes one or more target tool paths, describing a plurality of routes for the excavation vehicle 115 and/or the excavation tool 170 to follow in order to excavate the site. Further details regarding target tool paths are described below in reference to FIG. 6. The excavation vehicle 115 enters the hole 406 at a default tool height 420. Following the set of instructions received from the computers 120, the excavation vehicle 115 follows the first target tool path 422 and adjusts 424 the tool to a grade position to grade the ground surface at a shallow depth. At the conclusion of the grading routine, the excavation vehicle 115 continues along the first target tool path 422 and adjusts 426 the tool to a dig position at a deeper depth below the ground surface than the grade position. After executing the digging routine, the excavation vehicle 115 adjusts 428 the tool to a check position to execute a volume check routine. From the volume check routine, the excavation vehicle 115 determines that the volume of earth in the tool is sufficient to be dumped, the excavation vehicle 115 navigates to the dump pile 410 and dumps 430 the contents of the tool. After dumping the contents of the tool, the excavation vehicle 115 returns 432 the tool to the dig position and proceeds to conclude the first target tool path 422.

Excavating the hole 406 may involve multiple target tool paths, so at the conclusion of a first, shallower target tool path 422, the excavation vehicle 115 resets 434 the tool to the grade position follows a second, deeper target tool path 436 and adjusts 438 the tool to a second dig position to dig at that second, greater depth. The excavation vehicle 115 then follows the same process outlined above, adjusting 440 the tool to the same (or a different) check position, dumping 430 the contents of the tool, and returning 442 the tool to the second dig position. Further details regarding the digital file, grading routines, and digging routines are described below in reference to FIG. 6-8.

Figure 5:
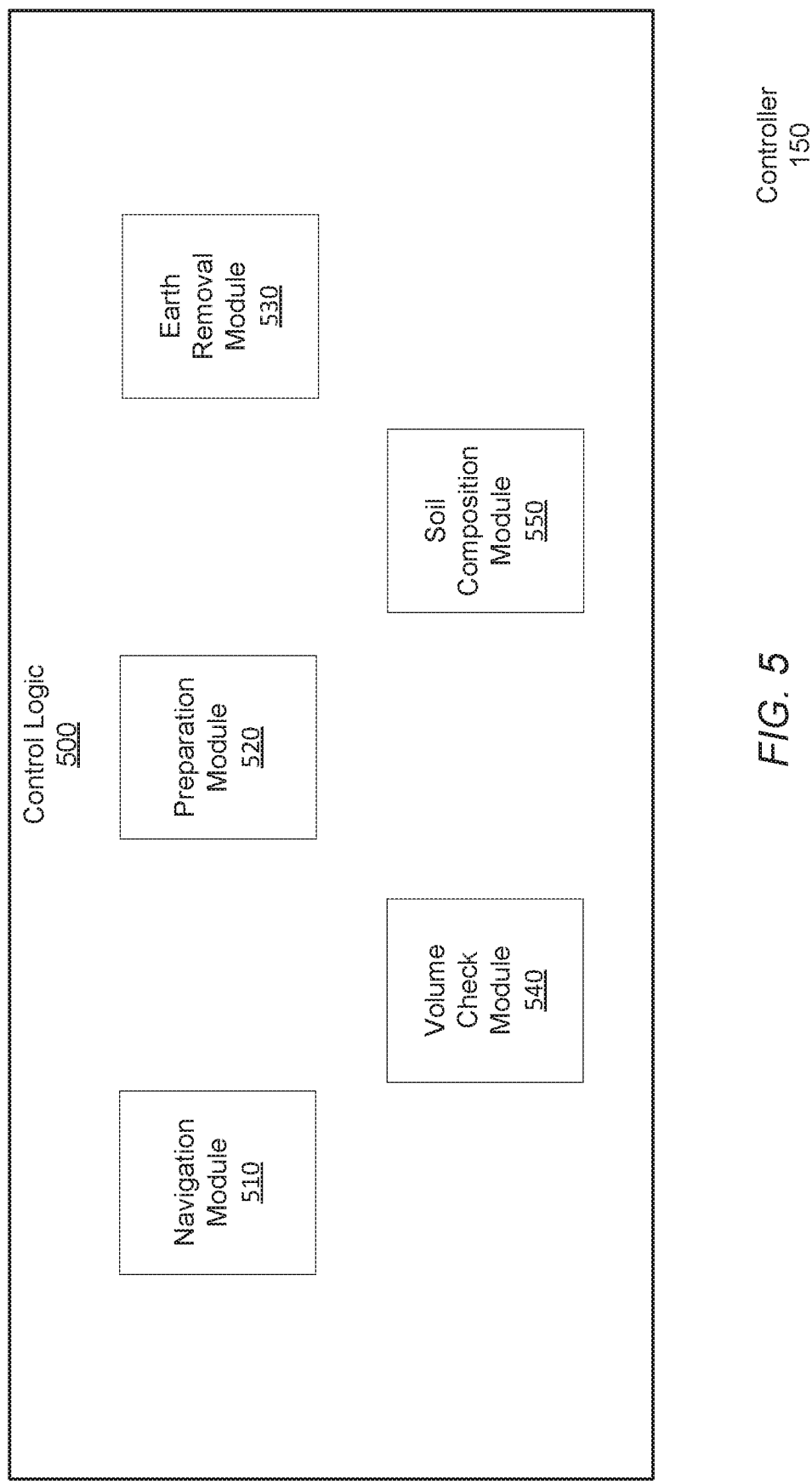
FIG. 5 is a diagram of the logical architecture for controlling an excavation vehicle, according to an embodiment.

FIG. 5 is a diagram of the system architecture for the control logic 500 of an excavation vehicle 115, according to an embodiment. The control logic 500 is implemented by software within the on-unit computer 120*a* and is executed by providing inputs to the controller 150 to control the control inputs of the vehicle 115 such as the joystick. The system architecture of the control logic 500 comprises a navigation module 510, a preparation module 520, an earth removal module 530, a volume check module 540, and a soil property module 550. In other embodiments, the control logic 500 may include more or fewer modules. Functionality indicated as being performed by a particular module may be performed by other modules instead.

The navigation module 510 is responsible for providing mapping and orientation instructions to the drivetrain 210 of the excavation vehicle 115, allowing the vehicle to navigate through the coordinate space of the site and along the target tool paths within the hole. The preparation module 520 creates and/or converts the digital file describing the target state of the site into a set of target tool paths describing the excavation of the hole, along with any other instructions needed to carry out the excavation routine such as navigation between the target tool paths and the dump site. The earth removal module 530 executes instructions to perform digging routines in order to physically excavate earth from the hole. The volume check module 540 measures the volume of earth within the tool and makes a determination regarding whether or not the excavation vehicle 115 should release the contents of the tool or continue excavating the hole. The soil property module 550 uses the sensor assembly 110 to record data describing the earth surround the excavation vehicle 115, extrapolates properties of the earth, and considers those properties when proceeding with the excavation routine.

III. Dig Site Preparation Routine

Figure 6A:
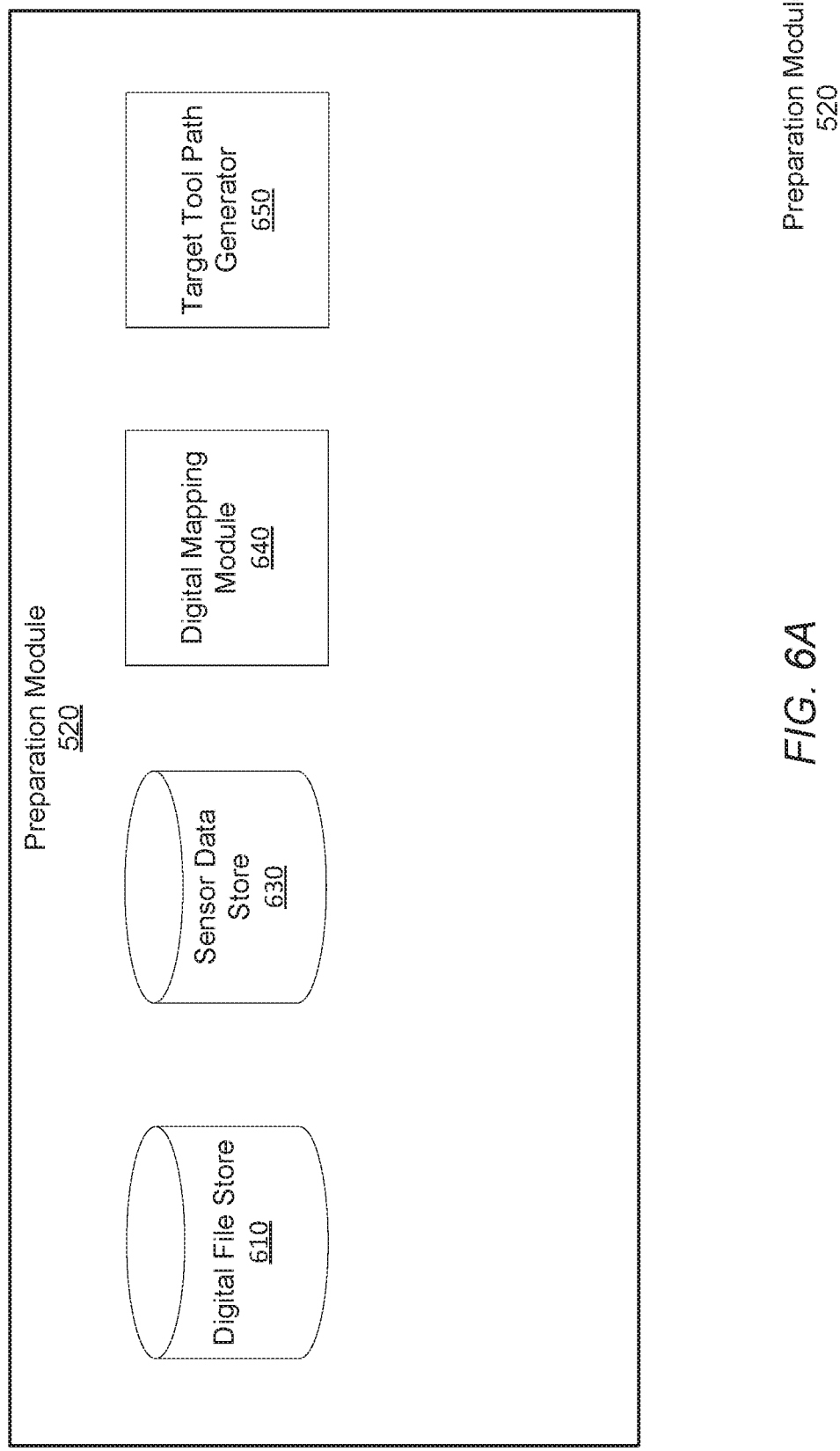
FIG. 6A is a diagram of the logical architecture for the preparation module, according to an embodiment.

FIG. 6A is a diagram of the system architecture for the preparation module 520 of an on-site or off-unit computer 120, according to an embodiment. The preparation module 520 generates a digital terrain model detailing one or more plurality of target tool paths which can be followed by the excavation vehicle 115. The system architecture of the preparation module 520 comprises a digital file store 610, a sensor data store 620, a digital mapping module 630, and a target tool path generator 640. In other embodiments, the preparation module 520 may include more or fewer modules. Functionality indicated as being performed by a particular module may be performed by other modules instead. Some of the modules of the preparation module 520 may be stored in the control logic module 500.

The digital file store 610 maintains one or more digital files, accessed from a remote database. Digital files may be represented as image files describing the geographic layout of the site as a function of location within the coordinate space of the site, with different images representing a hole, dump pile, an entry ramp, etc. Geographic locations in the coordinate space may be represented as one or more two or three dimensional points. The digital file may also include data describing how the excavation vehicle 115 ought to interact with each location discussed in the digital file. The digital files stored in the digital file store 610 may also include a digital file representing a target state of the site once all excavation has been completed. Digital files may be constructed using known computer programs and file types, such as a Computer Aided Design (CAD) file or a Building Information Modeling (BIM) file.

For example, the hole may be characterized by a set of target volume dimensions which should be achieved upon the conclusion of the excavation routine. At a boundary of the hole, the digital file may also include a ramp. Geometrically, the width of the ramp is generally greater than the maximum width of the combination of the excavation vehicle 115 and the tool. The location of the dump pile may be extracted from the digital file or received manually from a human operator. Alternatively, the location of the dump pile within the site may be based on the estimated maximum size of the dump pile and a specified relative distance between the dump pile and the hole and other equipment in the site. The placement of the dump pile is based on several considerations including: the risk of excavated earth caving in above the hole, the volume of excavated earth required to form the planned hole, the estimated compaction factor of the excavated earth, and the estimated swell factor of the excavated earth.

When appropriate, the digital file may also describe the location of fiducials representing technical pieces of equipment previously placed at the site such as stakes with active emitters and grade stakes. In alternate instances, the locations of the fiducials may be manually input to a computer 120 based on the records of a human operator.

A representation of the initial state of the site is generated using sensor 170 data, stored within the sensor data store 620. As the navigation module 510 maneuvers the excavation vehicle 115 through the site, sensors 170 gather contextual information on the site which is aggregated into a representation of the current state of the site. More specifically, spatial sensors 130 record spatial data in the form of point cloud representations, imaging sensors 135 gather imaging data, and depth sensors 145 gather data describing relative locations. The recording of contextual information is further described below in reference to FIG. 6B.

The digital mapping module 630 generates digital terrain models based on a comparison between the representation of the target state of the site, accessed from the digital file, and the representation of the initial state of the site, accessed from the contextual data. By aligning in the coordinate space of the site, the target state of the site with the initial state of the site, differences between the two representations can be identified by the computer 120. For example, the computer 120 may determine a volume of earth to be excavated to form the planned hole from the digital file. In one embodiment, the two representations (the digital file and the contextual data) are aligned (or register) using the known locations of fiducials and other locations within the site common to both representations. Position data from a position sensor 145 such as a GPS may also be used to perform the alignment. Algorithms, such as Iterative Closest Point (ICP) may be used to align the two representations. The boundaries of the sites provided by both representation may also be used to perform the alignment. In one embodiment, for every point pair in the actual/target representations, if the difference in elevation (e.g., Z-axis relative to the ground plane) is greater than a threshold, it is multiplied by the resolution of the representation to calculate a voxel volume, and is then summed together. This can performed at multiple points to determine how the two representations should be adjusted relative to each other along an axis to align them.

The digital terrain model also includes nuanced considerations for the excavation of the planned hole such as implementing one or more cutbacks and slope backs, as described in the received digital file. Cutbacks describe the raised surfaces within the planned hole and slope backs describe the sloped incline of the boundaries of the planned hole. The implemented target tool paths incorporate the creation of the one or more cutbacks and slope backs within the planned hole. Further, to generate the cutbacks, the tool may collect a volume of earth and use one or more sensors to obtain a soil cohesion measurement based on the collected volume of earth. Based on various soil properties, described in further detail below, the computers 120 may access a soil cohesion measurement from a remote server. Based on the received soil cohesion measurements, the computers 120 generate one or more geometric parameters describing the cutback and incorporate those parameters into the digital terrain model. The digital mapping module 630 may also receive information describing the potential locations for any human operators within the hole and adjusts the geometric parameters for the cutback based on these locations. For example, if a human operators will not be entering the hole, the cutback angle at that edge is smaller compared to if a human is planning on entering the hole. Additionally, the digital mapping module 630 receives an estimate of the length of time for the site to be excavated and, to prevent cave-ins, updates the instructions for the cutback accordingly.

Using the digital terrain model, the target tool path generator 640 generates one or more target tool paths for the excavation vehicle 115 to move a tool over in order to excavate the volume of earth as part of an excavation routine. As introduced earlier, tool paths provide geographical steps and corresponding coordinates for the excavation vehicle 115 and/or excavation tool to traverse within the site. When the site is represented in the digital terrain model as a coordinate space, as described above, a target tool path include a set of coordinates within the coordinate space. A target tool path may further represents a measure of volume relative to the volume of the planned hole. For example, if a hole is 4" wide, 3" long, and 2" deep, a single target toolpath includes coordinates within the 12" area of the coordinate space and, at each coordinate, places the tool at a depth of 2" in order to excavate the hole using a single target tool path. Target tool paths may describe a variety of shapes representing a variety of excavation techniques, for example substantially rectangular pathways in two dimensions, substantially triangular pathways in two dimensions, hyperrectangular pathways in three dimensions, hyperrectangular pathways in three dimensions, elliptic pathways in two dimensions, hyperelliptic pathways in three dimensions, or curved lines along the plane of the ground surface.

Some target tool paths achieve goals other than digging. For example, the last target tool path used at the conclusion of the excavation of the hole may be referred to as a finish tool path, which digs minimal to no volume and which is used merely to even the surface of the bottom of the dug hole. While moving through the finish tool path, the tool excavates less earth from the hole than in previous target tool paths by adjusting the depth of the leading edge or the angle of the tool beneath the ground surface. To conclude the digging routine, the excavation vehicle 115 adjusts a non-leading edge of the tool and reduces the speed of the drive.

For holes of greater volumes or requiring a graded excavation, multiple target tool paths may be implemented at different offsets from the finish tool path. For example, if three target tool paths are required to excavate a 6" deep hole, the first may be executed at a depth of 3", the second at a depth 2", and the third at a depth of 1". As a result, a target tool path may represent only a fraction of the volume of excavated earth. In one embodiment, the number of target tool paths may be calculated by dividing the target depth of the hole by the maximum depth that each tool path is capable of. In some instances, the maximum depth that each tool path is capable of is also defined by the dimensions of the tool 175 attached to the excavation vehicle 115. In other embodiments, the target tool paths may be manually generated using the off-unit computer 120*b*.

Additionally, target tool paths may not describe the shape of the hole in three-dimensions, instead removing the depth measurement to only specify a two-dimensional pathway or two-dimensional plane in the three or two dimensional coordinate system. In such instances, the depth instructions for how deep to dig with a target tool path may be provided for separately in the set of instructions.

Target tool paths are defined based on several factors including, but not limited to, the composition of the soil, the properties of the tool being used to excavate the hole, the properties of the drive system 210 moving the tool, and the properties of the excavation vehicle 115. Soil composition properties are further described below in reference in Section IV.D. Example properties of the excavation tool 175 and excavation vehicle 115 include the size of the tool, the weight of the excavation tool, and the force exerted on the excavation tool 175 in contact with the ground surface of the site.

Figure 6B:
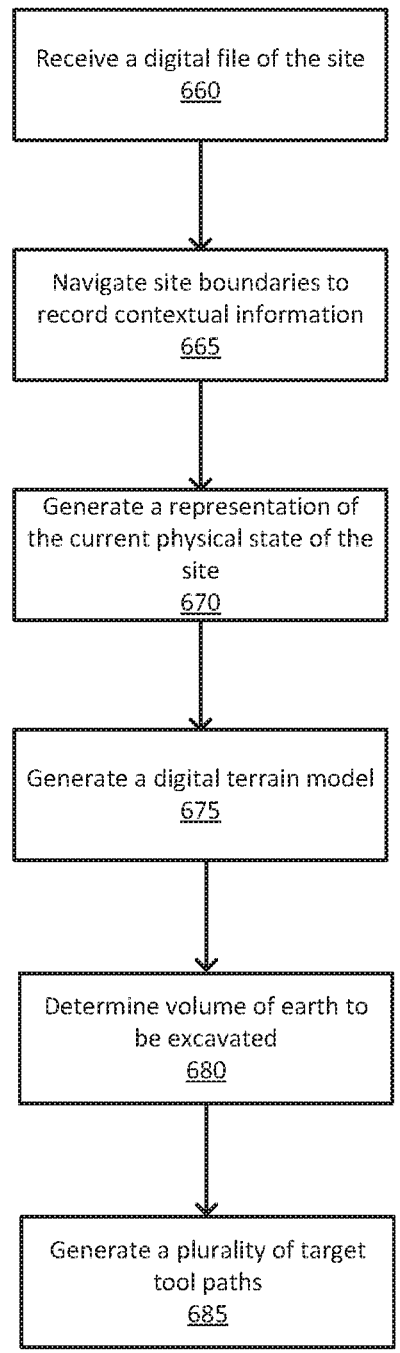
FIG. 6B shows a flowchart describing the process for an excavation vehicle to prepare a digital terrain model of a dig site, according to an embodiment.

To implement the system architecture of the preparation module, FIG. 6B shows an example flowchart describing the process for a preparation module 520 to prepare a digital terrain model of the site, according to an embodiment. As described above, a digital file of the site detailing planned excavation of a hole and the area surrounding the hole is received 660 by the controller 150 and stored within the digital file store 610. In some instances, the controller 150 may access these digital files from an off-unit computer 120*b* and subsequently store them in the digital file store 610.

The navigation module 510 navigates 665 within the geospatial boundaries defined by the digital file to record contextual information describing the current state of the site. The navigation of the excavation vehicle 115 within the coordinate space of the site is guided by the navigation module 510. Contextual information refers to the physical landscape of the site and the physical properties of the soil within the site. The contextual information, stored in the data store 620, is recorded using the system of sensors, such as spatial sensors and imaging sensors. When recording data via one or more spatial sensors, the spatial sensors 130 record one or more photographic images of various portions of the site and stitches the recorded images into one or more point clouds of data representing the portions of the site to generate 670 a representation of a current physical state of the site. Additionally, for each of the recorded images, the position and orientation of features within the site are recorded and translated into the point cloud representations with respect to the coordinate space of the digital file. In alternative instances, the sensor assembly 110 uses an imaging sensor 135 to record the contextual information as photographic images of portions of the site and, for each of those images, stores the associated positions and orientations of the relevant features within the portion of the site. In another implementation, the excavation vehicle 115 includes sensors and a software assembly that generates a digital terrain model of the site using simultaneous localization and mapping (SLAM).

Using the generated representation of a current physical state of the site and representation of the target state of site to generate 675 a digital terrain model of the site. As described earlier, the digital terrain model is generated by the digital mapping module 630 by aligning the two representations by common features such as physical fiducials within the sites or the boundaries of the site.

Using the digital terrain model, the computers 120 determines 680 the volume of earth to be excavated based on the differences between the representation of the current state of the site and the target state of the site. More specifically, using the digital terrain model, the computers 120 determine 680 the difference in volume between the two representations which translates into the volume of earth to be excavated from the hole. Incorporating all the considerations made above, the physical layout of the site, the volume of earth to be excavated, and the creation of cutbacks and slope backs, the computer 120 generates 685 one or more target tool paths. Finally, the computers 120 receive the digital terrain model, generate, and deliver a set of instructions for controlling the tool as it follows the one or more target tool paths.

When executed in reverse or in alternative sequences, the processes described above and below with respect to digging and grading as specific examples may also perform other excavation routines including, but not limited to, filling, trenching, compacting, aerating, ripping, stripping, spreading, and smoothing.

IV. Earth Removal Routine

Figure 7A:
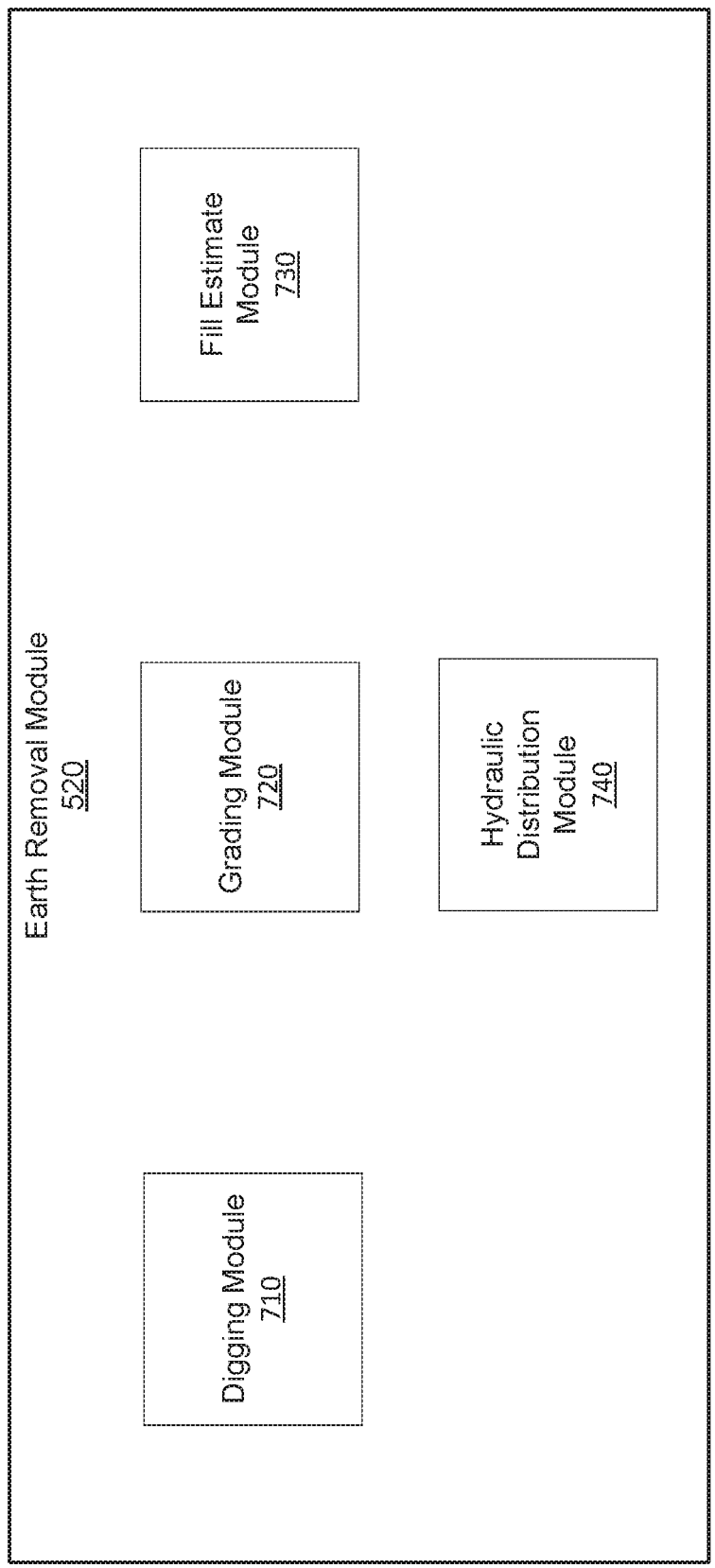
FIG. 7A is a diagram of the logical architecture for the earth removal module of, according to an embodiment.
Figure 7B:
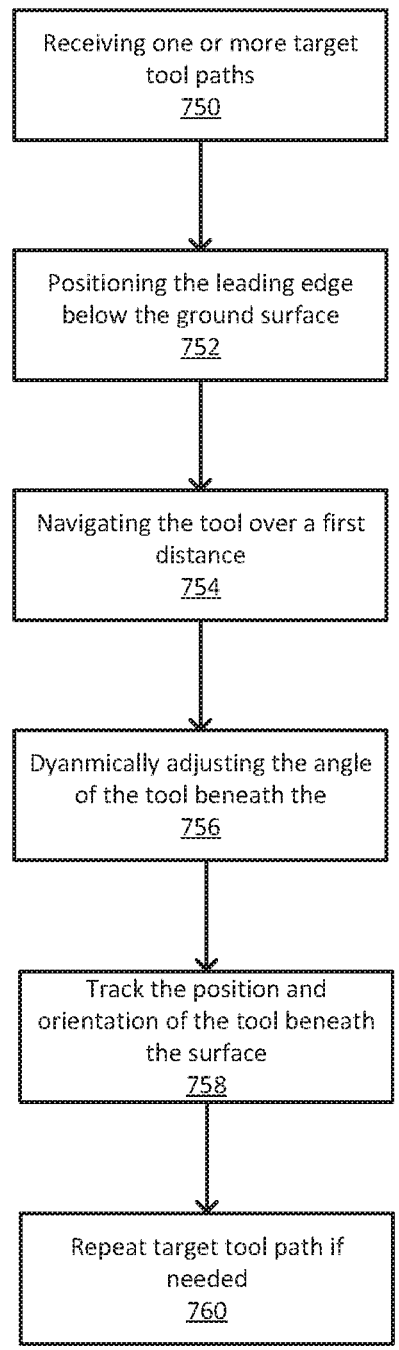
FIG. 7B shows a flowchart describing the process for an excavation vehicle to execute a grading routine, according to an embodiment.

FIG. 7A is a diagram of the system architecture for the earth removal module of an excavation vehicle 115, according to an embodiment. The earth removal module 530 executes a set of instructions for guiding the tool through an excavation routine to excavate earth from the hole. The instructions cause the controller 150 to control the tool 175 to be lowered into contact with the ground surface and then advanced (directly or indirectly by moving the entire vehicle 115 with the drive train 210) forward to excavate earth from the ground into the tool. The system architecture of the earth removal module 530 comprises a digging module 710, a grading module 720, a fill estimate module 730, and a hydraulic distribution module 740. In other embodiments, the earth removal module 530 may include more or fewer modules. Functionality indicated as being performed by a particular module may be performed by other modules instead. Some of the modules of the earth removal module 530 may be stored in the control logic module 500.

The digging module 710 executes a digging routine to excavate a volume of earth from the planned hole, consistent with a provided set of instructions and the target tool path. The digging module 710 executes a digging routine by accessing the one or more target tool paths of an excavation routine, for example as generated by the preparation module 520, and moves the tool 175 and/or vehicle 115 accordingly. The digging module 710 may also continuously or periodically track the position of the tool within the coordinate space using information obtained from the position sensor 145.

The grading module 720 executes a variation of the digging routine, executed by the digging module 710 to grade an excavated surface by lowering the leading edge of the tool and maintaining it at a depth shallower than the depth of the digging routine. The grade routine may be performed prior to, in the middle of, or at the conclusion of the digging routine (e.g., as a finish target tool path as described above). Additionally, when grading, the grading module 720 may instruct the excavation vehicle 115 to dump or push excavated earth into low points within the grade area of the hole to smooth out hollowed sections of the hole, not prescribed by the target tool path. Filling of such low spots may be done by using an excavation tool to release earth in the holes or by using a dozer blade to push earth from a high point to a low point.

The fill estimate module 730 determines an estimate of the volume of earth in-situ as the tool is moved over a distance along the target tool path. The fill estimate module 730 compares the estimate to a threshold volume of earth. When the estimated volume is greater than the threshold volume, the fill estimate module 730 halts the digging routine and raises the tool above the ground surface and executes a check routine to better estimate the amount of earth currently in the tool.

The hydraulic distribution module 740 monitors and adjusts the distribution of hydraulic pressure from the engine that is allocated between the drive system 210 and tool 175. The hydraulic distribution module 740 does this in response to instructions from another module (such as the digging module 710) attempting to carry out the excavation routine, as control of the hydraulic pressure dictates the actuation of the tool 175 and movement of the vehicle 115. In practice, the digging module 710 may specify some device parameter to be maintains, such as the tool 175 breakout angle, and the hydraulic distribution module 710 sets the hydraulic distribution between the tool 175 and drive system 210 to maintain that breakout angle. The breakout angle refers to the threshold angle of the tool at which the tool is capable for breaking through the ground surface during the digging routine.

IV.A. Digging Routine

In one implementation, the navigation module 510 moves the tool forward through the hole within the site to excavate earth from the hole. The digging module 710 receives 750 the one or more target tool paths generated by the preparation module 520 and positions 752 the leading edge of the tool below the ground surface. The depth below the ground surface at which the tool is placed is guided by the set of instructions received from the controllers 120.

In addition to defining the height at which the leading edge is lowered beneath the ground surface, the set of instructions may also instruct the navigation module 510 how far to move 754 the tool along the target tool path without raising the tool above the ground surface. In order to maintain the movement of the tool beneath the ground surface, the digging module 710 dynamically adjusts 756 mechanical conditions of the excavation vehicle 115 including, but not limited to, the angle of the tool beneath the ground surface, the torque output of the engine system, and the true speed of the tool. The angle of the tool beneath the ground surface can be adjusted to reduce the rate at which the tool collects excavated earth. For example, when the tool is angled perpendicular to the flat ground surface, the rate of excavation may be at its highest. Alternatively, when the tool is angled parallel to the flat ground surface, the rate of excavation may be at its lowest. Additionally, at lower speeds, the tool is generally often better able to maintain the angle optimal for excavating earth.

While moving through the excavation routine for the planned hole, the digging module 710 tracks 758 the position and orientation of the tool within the coordinate system using the position sensors 145 physically mounted on the excavation vehicle 115 as described above in reference to FIG. 3A-3B. The orientation of tool, described in reference to the angle of the tool relative to a reference orientation, is recorded using one or more position sensors 145. Examples of reference orientations include the ground surface, a gravity vector, or a target tool path. As the tool is moved along the target tool path, the soil may push the leading edge to a neutral to the angle of the reference orientation, at which point the tool is raised above the ground surface.

To track 758 the positioning of tool beneath the ground surface, the digging module 710 may utilize several methods to record the relative position of the leading edge within the coordinate space of the digital terrain model of the site. In some implementations, the relative position of the leading edge is recorded relative to the position of the excavation vehicle within the site. Examples of the methods used to track the relative position of the leading edge include, but are not limited to, using a global positioning system mounted to the tool, using an measurement sensor mounted to the excavation tool 175, using a linear encoder mounted to the excavation vehicle 115, measuring the pressure on the hydraulic system controlling the tool, using a spatial sensor mounted to the excavation vehicle 115. Additionally, the digging module 710 may use a sensor (such as a measurement sensor) mounted to the excavation vehicle 115 to measure the relative position of the tool and convert that measurement into an absolute position using a lookup table stored by the computers 120 or by using forward kinematics characteristic of the excavation tool and the soil composition surrounding the site. The sensor assembly 105 may also measure the quantity of earth in the bucket or the quantity of earth remaining in the site, and use that information along with information from the digital terrain model to determine the absolute position as a function of the amount of earth removed/remaining.

As the tool moves along a target tool path, soil friction and soil composition factors may result in tool deviating from the target tool path, creating an actual tool path that was travelled by the tool 175 or vehicle 115. Because of the deviation between the target tool path and the actual tool path, the actual tool path is associated with a different set of coordinates within the coordinate space than those associated with the target tool path. In one embodiment, the digging module 710 repeats 760 the same target tool path until a deviation between the target tool path and the actual tool path is less than a threshold deviation, or until some other outcome is achieved, such as a threshold amount of earth is removed. Alternatively, if the deviation between the target tool path and the actual tool path is below a threshold deviation, the excavation tool executes the next portion of the excavation routine which may be a check routine, a dump routine, or second (e.g., deeper) target tool path. Periodically while moving through the actual tool path, the digging module 710 updates the tool fill level and records the speed of both the tool and the drive system. Based on these recorded considerations, the digging module 710 either continues to move the tool through the earth or exits the digging routine to execute a check routine. With the conclusion of an actual tool path, the controller 150 may update the tool fill level, before continuing with the excavation routine for the planned hole.

The digging module 710 can also determine that the target tool path is obstructed by one or more obstacles, for example rocks, trees, roots, wooden beams, buried pipelines, cables, pieces of concrete, asphalt, and steel. Determinations regarding the presence of obstacles along the tool path are made based on occurrence of one or more of a set of conditions, including, but not limited to, an engine load greater than the target engine load, a ground speed lower than the minimum ground speed, and a tool angle lower than a target tool angle. These inputs may be received by the sensors 170 and passed to the on-unit computer 120a for evaluation by the digging module 710.

When an obstruction is determined to be within the target tool path, the digging module 710 may store the geospatial location of the obstacle, for example a current location of the vehicle 115 as provided by the position sensor 145, execute a dump routine to release earth from the tool, and return to the location of the obstacle within the site to execute a break routine to hopefully break up and/or remove the object.

Break routines, in one embodiment, include instructions to the controller to repetitively drive the leading edge of the tool downward into the earth around the location of the obstacle, running the leading edge of the tool over the location of the detected obstacle to "scrape" or loosen this earth, and activating an alternate tool (not shown) to break down the obstacle. In another embodiment, after determining that an obstacle lies within the target tool path, the earth removal module 530 may halt the digging routine until a human operator can manually operate this 115 or another excavation vehicle to remove the object.

IV.B. Grading Routine

In addition to finishing target tool paths and possibly separately from a digging routine, the grading module 720 may execute a grading routine to perform grading tasks. A grading routing may, for example, include moving the tool forward through the hole to grade the ground surface of the hole, where the tool is set at a shallow or zero depth position relative to the aggregate or average ground plane. At such a shallow depth, the tool requires less forward force from the drive system 210 to move the tool forward than when the tool is lowered to a greater, digging-oriented depth. This allows the excavation vehicle 115 to be fitted with a tool suited to grading, such as a tool of greater volume relative to a digging routine oriented tool, which would be able to hold a greater amount of earth within the mechanical and hydraulic constraints of the excavation vehicle 115 and while also requiring fewer dump routines for dumping excess graded earth.

Figure 7C:
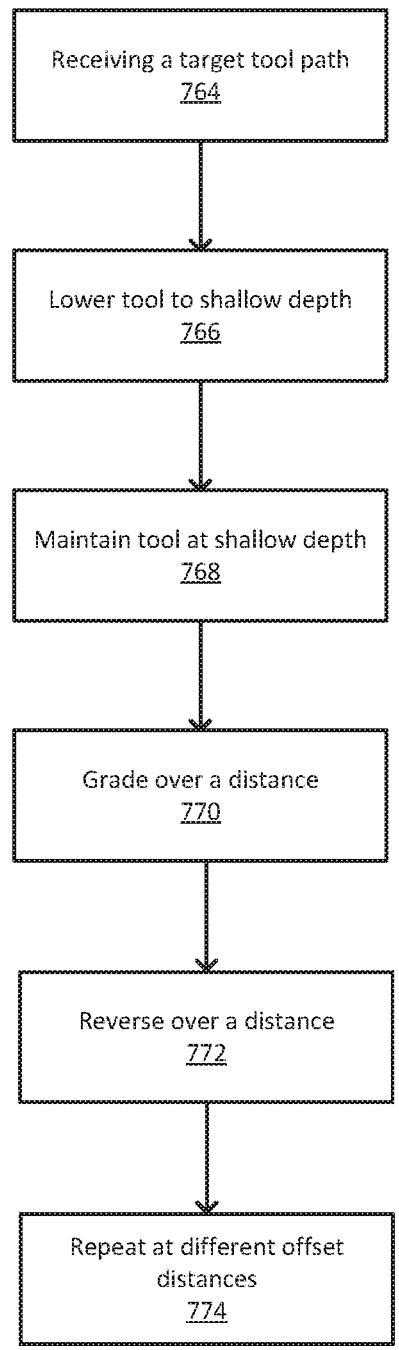
FIG. 7C shows a flowchart describing the process for an excavation vehicle to execute a digging routine, according to an embodiment.

FIG. 7C shows a flowchart describing the process for an excavation vehicle 115 to grade a surface using a grading routine. The grading module 720 receives 764 a target tool path and the set of instructions describing the grading routine and lowers 766 the tool to a grading depth at or beneath the ground surface, and maintains 768 the tool at this shallow to zero depth to grade 770 along the target tool path. Grading of the ground surface may result in an uneven ground surface when the tool moves in a first direction, so the grading module 720 may further cause the tool to be moved in a reverse 772 direction, and possibility additional one or more further times over the coordinates previously graded. Once the grading has been completed based on a set of target conditions included in the set of instructions, the grading module 720 may repeat 774 the grading process at various tool offsets further excavate or grade areas of the site as needed.

IV.C. Fill Level Estimate Routine

Figure 7D:
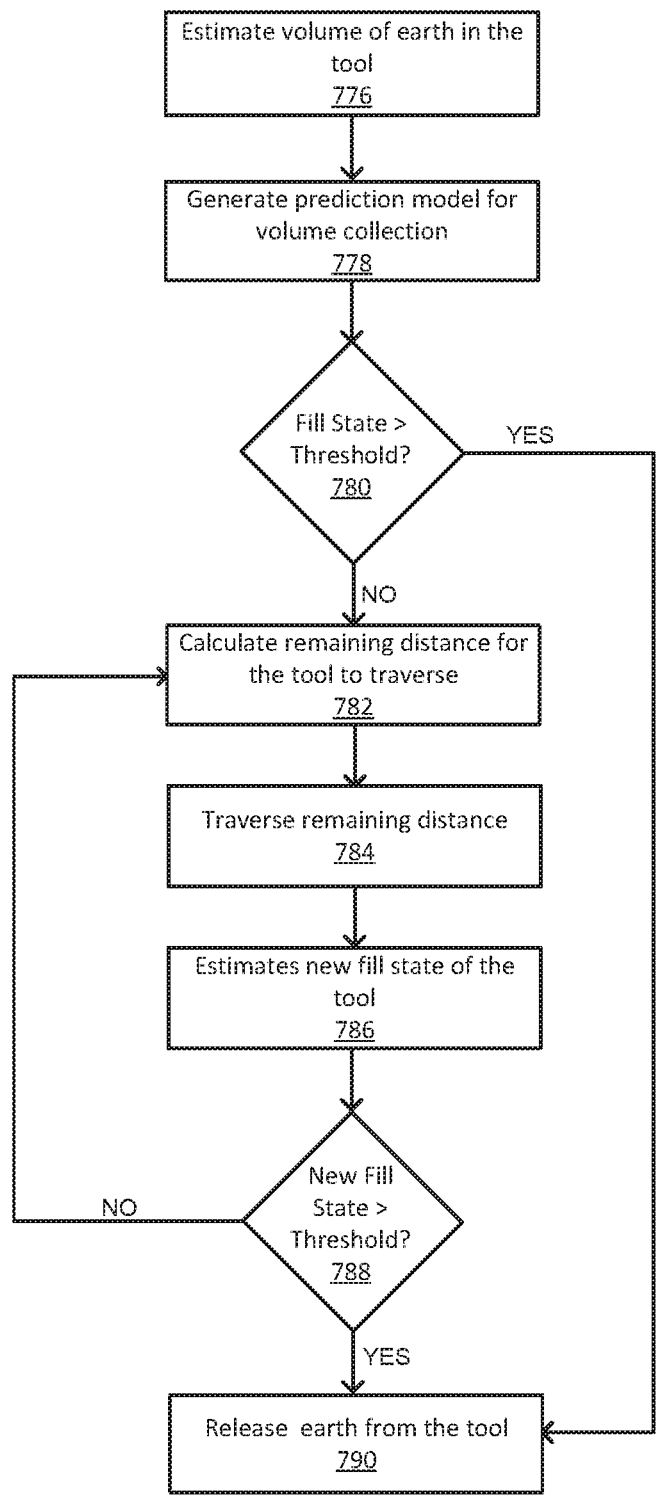
FIG. 7D shows a flowchart describing the process for an excavation vehicle to execute a fill estimate routine, according to an embodiment.

Prior to executing a check routine and going to the trouble of interrupting a target tool path execution and raising the tool above the ground surface, a digging routine may include executing a fill estimate routine by estimating the tool fill level without interrupting the movement of the tool within the target tool path. FIG. 7D shows a flowchart describing the process for the fill estimate module 530 to execute a fill estimate routine, according to an embodiment.

The fill estimate module 730 estimates 776 a fill level of the tool using any one or more of a number of techniques. The fill level of the tool describes the volume of earth in the tool. One technique estimates the volume by mathematically integrating the depth of the leading edge beneath the ground surface over the distance traveled by the tool over the target tool path. In another technique, the fill estimate module 730 uses the point cloud representation of the current state of the site gathered using one or more spatial sensors to determine a pre-excavation volume of earth in the hole and accesses, from the computers 120 or a remote server, a swell factor of the earth relating the volume of earth in the tool to the pre-excavation volume of earth in the hole. Using the pre-excavation volume of earth in the hole and the swell factor characteristic of the earth, the fill estimate module 730 may estimate the volume of earth in the tool. In another technique, the fill estimate module 730 uses the sensor assembly 105 to measure the quantity of earth accumulated in front of the leading edge of the tool while the tool is in the position set by the currently-in-progress target tool path. The fill estimate module 730 may also use measurement sensors to measure the force of earth acting on the tool beneath the surface and adjust the angle of the tool to estimate the fill level of the tool.

As another technique, the fill estimate module 730 may access 778 a previously trained prediction model that is capable of receiving as input the distance traveled by the tool along with other parameters of the vehicle 116 and excavation routine and outputting an estimated amount of earth in the tool. These other parameters include, but are not limited to, any sensor value, the tool type and width, the vehicle type, and the depth of the leading edge of the tool below the ground surface during the target tool path. The trained prediction model may further be capable of generating a trend line that extrapolates tool fill level as a function of distance traveled, which may in turn be used to generate an estimate when to initiate a check or dump routine. Alternately, the prediction model may generate such an estimate directly.

The fill estimate module 730 compares 780 the fill estimate to a threshold volume. The threshold volume may be the maximum available volume of the tool, a volume set manually by a human operator, a volume set by a calibration procedure using the tool in an empty state, or another volume.

When the estimated volume is greater than the threshold volume, the excavation vehicle measures the angle of the tool beneath the ground surface, adjusts the angle of tool towards the breakout angle, and raises the tool above the ground surface. Alternatively, when the estimated volume is less than the threshold volume, the fill estimate module 730 may simply continue the digging routine. However, in one implementation the fill estimate module 730 calculates 782 the remaining distance for the tool to traverse in order to be filled at maximum capacity using a trend line generated by the prediction model. Based on the available volume in the tool, the trend line is inputted into the prediction model to determine the remainder distance on the target tool path that the tool needs to travel to be filled at maximum capacity.

As previously described, in some implementations the fill estimate module 730 measures the quantity of earth accumulated in front of the leading edge. When the measured quantity of earth is above a threshold quantity, the excavation vehicle raises the tool above the ground surface. Similarly, the fill estimate module 730 may measure the force of earth acting on the tool beneath the ground surface and, when the measured force of earth is above a threshold quantity, the excavation vehicle raise the tool above the ground surface.

After calculating the remaining distance to be traveled, the fill estimate module 730 traverses 784 the remaining distance and estimates 786 a new volume of earth in the tool. As with the previous volume estimate, the updated volume estimate is compared 788 to the threshold volume. This process may be repeated multiple times. When the estimated volume is greater than the threshold volume, the controller 150 executes a dump routine and releases 790 earth from the excavation tool. The dump routine is further described below in reference to FIG. 8A-8B.

Alternatively, the controller fill level estimate module 730 estimates the volume in the tool to be below a threshold value and repeats the target tool path without calculating a remaining distance. The tool fill level may be periodically measured and the target tool path may be repeated until the updated volume estimate is greater than the threshold volume.

IV.D. Hydraulic Distribution Adjustment

Maintaining the tool at a desired angle or depth through the carrying out of a target tool path is a non-trivial task, and the hydraulic distribution module 740 is configured to adjust the hydraulic capacity allocated to the drive system and tool path dynamically to control the controller 150 in achieving the target tool path. Generally, the excavation vehicle only has sufficient hydraulic pressure to power a single system at full capacity. As a result, both the drive and tool systems may be powered equivalently at half capacity. However, if, based on soil friction, forces, speeds, tool angles, or other conditions, the angle and depth of the tool cannot be maintained at half capacity, the hydraulic distribution module 740 may redistribute the hydraulic pressure within the system to favor the tool over the drive system (e.g., 75%-25% distribution, or otherwise). The calibration for the hydraulic system may be performed by observing joystick manipulations within the excavation vehicle and recording the changes in pressure distribution. The remainder of this section describes a number of example operating conditions that can trigger hydraulic pressure adjustments and what those adjustments are.

In moving the tool through the target tool path, the hydraulic distribution module 740 measures the speed of the tool and compares it to a target speed. The target speed refers to the speed that the drive system 210 is traveling. This may be calculated based on the knowledge of the earth of the site exhibiting an industry standard soil friction or a soil friction determined specifically for the excavation vehicle 115, site, or even specific target tool path being executed. If the measured speed is lower than the target speed, the hydraulic distribution module 740 may determine that the soil friction (or force of soil exerted on the tool) is greater than expected, and adjusts the distribution of hydraulic pressure between the drive system and the tool to favor the tool to reduce the increase the speed of the tool. While this may be accomplished in some instances by increasing the amount of hydraulic pressure capacity allocated to the drive system, the amount of hydraulic capacity available is finite and so this is not always a viable solution. Often, greater than expected soil friction is due to the tool being too deep (or angled along a path proceeding downward), thus generating more friction and often causing the tool to fall off the target tool path. To compensate, the hydraulic distribution module 740 may adjust the tool to a shallower depth or angle, which will accomplish reducing the soil friction and raising tool speed. This process may play out in reverse for a tool speed greater than expected, which may be adjusted by lowering the tool or setting it at a deeper angle.

The maintenance of the hydraulic capacity in this manner and as described elsewhere herein prevents the excavation from stalling during the excavation routine or from complications regarding raising the excavation tool above the ground surface. In one embodiment, to further maintain sufficient hydraulic capacity for it to be possible to make adjustments to the position and orientation of the tool during the digging routine, the hydraulic distribution module 740 maintains hydraulic pressure within the hydraulic system below a threshold 90% of the maximum hydraulic pressure capacity.

A breakout event and corresponding breakout angle may be recorded as a result of the tool naturally breaking through the ground surface during the digging routine. At speeds above the target speed and/or at forces above the threshold force, the tool is unable to collect earth and break out of the ground surface. Similarly, at speeds below the target speed and forces below the threshold force, the tool inefficiently collects earth. Breakouts and the speeds and forces that cause them are addressed by module 740 to resume digging if they do occur and hopefully reduce their occurrence overall. This may involve the hydraulic distribution module 740 measuring the force of earth on the tool and adjusting the distribution of pressure so that the tool angle has sufficient hydraulic pressure to be adjusted beneath the ground surface. The tool may be lowered or angled downward to dig more deeply in cases of high speed/low force, and angled upward/raised to dig more shallowly in cases of low speed/high force. Additionally, as the tool moves through the target tool path and collects earth, the excavation vehicle may continuously adjusts the angle of the tool and if the tool eventually breaks out of the ground surface, the excavation vehicle 115 records the breakout angle and may voluntarily opt to execute the volume check routine rather than resuming digging.

In advance of breakout occurring, the digging module 710 may also calculate the expected breakout angle based on the soil composition properties for the earth within the hole. Soil composition properties are further described below. During some digging routines, the breakout angle may be established as the minimum angle of the tool at rest during the digging routine. In one implementation, the breakout angle is established as inversely proportional to the soil cohesion measurement. In order to achieve the breakout angle as the tool is raised above the ground surface, the hydraulic distribution module 740 adjusts the distribution of hydraulic pressure between the drive system 210 and the tool 175 by monitoring engine load or line pressure sensors in the hydraulic system and dynamically adjusting power output commands to the drivetrain and to the tool actuators.

In another implementation, the difference in the set of coordinates for the actual tool path and the target tool path is greater than a threshold difference, the distribution of hydraulic pressure is adjusted to lower or raise the tool at a greater or lesser depth below the ground surface to better match the target tool path.

Additionally, the hydraulic distribution module 740 may use the received set of instructions to maintain the hydraulic capacity of the hydraulic system and decrease the target speed of the drive system 210 by adjusting the distribution of hydraulic pressures. A decrease in target speed results in a reduction of the overall hydraulic pressure in the hydraulic system, thereby ensuring sufficient scope in the hydraulic system to adjust the position and orientation of the tool and with minimal delay during the digging routine. For example, if the hydraulic pressure within the system is 98% of the maximum hydraulic pressure, exceeding the threshold hydraulic pressure, the hydraulic distribution module 740 can reduce the target speed of the excavation vehicle 115 by dynamically executing instructions to divert hydraulic pressure from the drivetrain to the set of tool actuators. By redistributing hydraulic pressure away from the certain components of engine system and towards other components of the engine system, the hydraulic distribution module 740 can prioritize certain excavation functions and maintain high excavation efficiency by the tool and excavation vehicle 115.

IV.E. Volume Check Routine

Figure 8A:
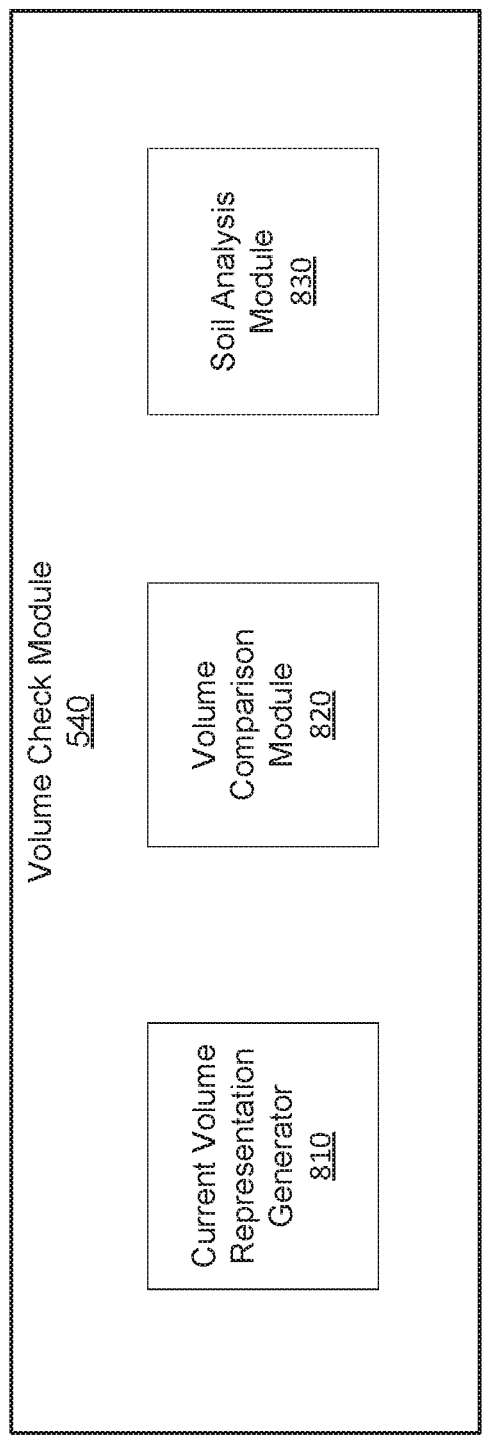
FIG. 8A is a diagram of the system architecture for the volume check module of an excavation vehicle, according to an embodiment.

FIG. 8A is a diagram of the system architecture for the volume check module 540 of an excavation vehicle 115, according to an embodiment. The volume check module 540 executes a set of instructions for measuring the volume of earth in the tool once raised above the ground surface and determining whether to continue moving the tool along the target tool path or to perform a dump routine of the earth within the tool. The system architecture of the volume check module 540 comprises a current volume representation generator 810 and a volume comparison module 820. In other embodiments, the volume check module 540 may include more or fewer modules. Functionality indicated as being performed by a particular module may be performed by other modules instead. Some of the modules of the volume check module 540 may be stored in the control logic module 500.

At a high level, the volume comparison module 820 compares a representation of the current fill state of the tool (e.g., in image or point cloud form) and an empty representation of the tool (in a comparable form) to determine the volume of earth within the tool. The empty representation of the tool may be generated during an off-run calibration procedure and stored in a memory of the computer for access and use as part of the check routine. Alternatively, the empty representation may be provided to the volume comparison module 820 manually by a human operator.

To accomplish this, the current volume representation generator 810 uses data recorded by the sensors of the sensor array 110 to generate a current representation of the fill state of the tool. The implemented sensors may include an imaging sensor, a spatial sensor, or some combination of the two sensors and the data describing the fill state of the tool may be represented as a point cloud or as image/s. To record the data, the volume check module 540 adjusts the tool to a measuring position at a height in the field of view of the one or more sensors. For example, the volume check module 540 can raise and tilt the tool to bring the interior volume of the tool into the field of view of the set of sensors. The volume check module 540 may confirm that the tool is in the measuring position by sampling data from the position sensors 145 mounted directly on the excavation tool 175 or within the hydraulic system. The volume check module 540 may also confirm that the tool is in the measuring position by analyzing images recorded by a system of depth and imaging cameras mounted to the excavation vehicle 115. If the distribution of earth within the tool is uneven, the check routine instructions may cause the volume check module 540 to shake the tool one or more times to achieve a more uniform distribution of the earth inside.

To determine the position of tool within the three-dimensional coordinate space, the current volume representation generator 810 may use the sensors 170 by measuring the quantity of earth in the tool and referencing a parametric model or lookup table to determine the position of the tool in the coordinate space. Lookup tables are generated by measuring the output of a sensors at various positions of the tool and correlating the two conditions. For example, at a depth of 1 meter, the tool is located at a position 4 meters perpendicular to the ground. The correlation between a depth measurement of 1 meter and a position measurement of 4 meters is stored within the lookup table. The referenced lookup table may differ depending on the type of sensor used and the format of the output provided. The current volume representation generator 810 may receive outputs from multiple sensors facing distinct regions of the interior of the tool.

Next, the current volume representation generator 810 generates a representation of the amount of earth currently in the tool based on the position of the tool within the coordinate space and the output of the sensor using one or more soil composition properties, for example the densities, sizes, shapes, and colors of the particles of the earth in the tool. The soil property module 550 analyzes data captured by the sensors 170 to determine the soil composition of the excavated earth within the tool.

In addition to the representation of the amount of earth in the tool, the excavation tool also accesses an empty representation of the tool calibrated prior to the execution of the digging routine. To calibrate the empty representation of the tool, the empty tool is adjusted to multiple heights and angles above the ground surface. For each of the heights and angles, the current volume representation generator 810 uses a sensor to record data describing the available volume within the empty tool. As described earlier, the recorded data and the respective height and angle measurements are stored in a lookup table to be referenced by the excavation vehicle 115. Depending on the sensor used to record the data, the contents of the lookup table may differ, for example a lookup table generated using a spatial sensor 130 includes a point cloud representation of the empty tool at various heights whereas a lookup table generated using an measurement sensor 125 includes a volume measurement of the empty tool at various heights.

Figure 8B:
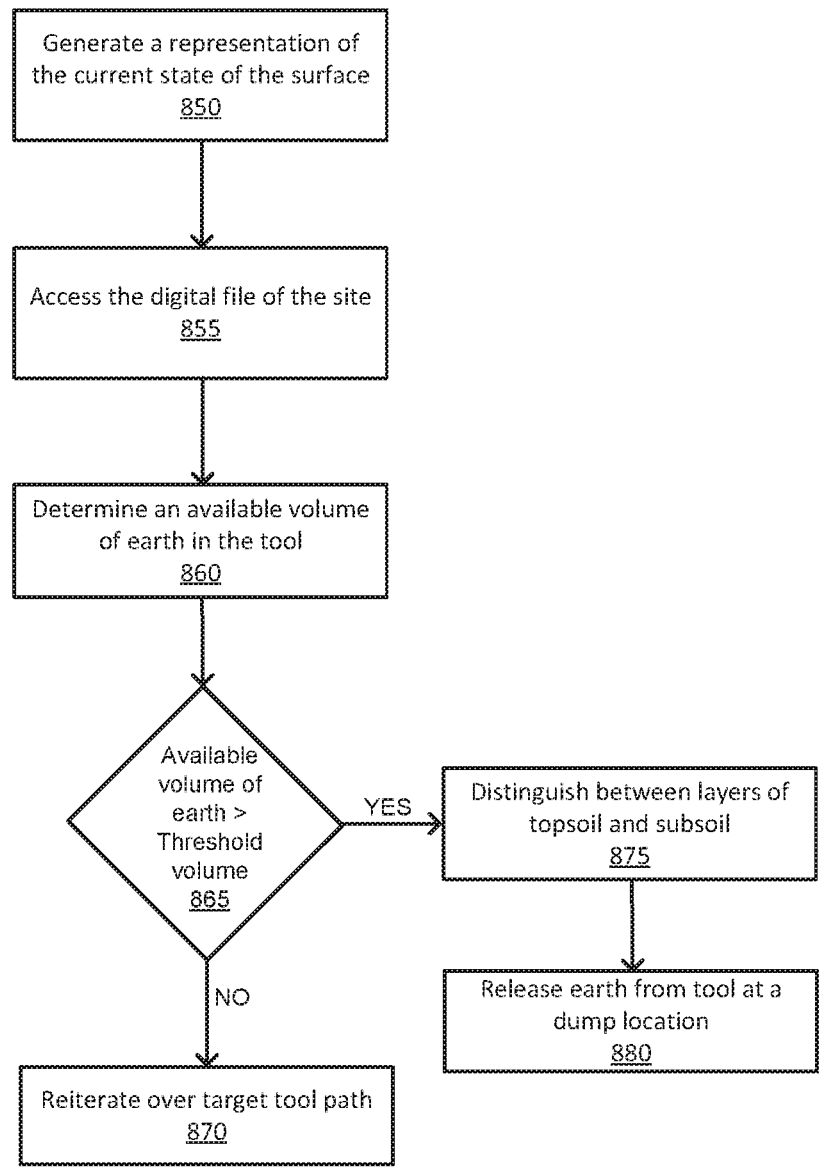
FIG. 8B shows a flowchart describing the process for an excavation vehicle to execute a volume check routine, according to an embodiment.

FIG. 8B shows a flowchart describing an alternate implementation for an volume check module 540 to execute a volume check routine. The current volume representation generator 810 generates 850 the representation of the amount of earth in the tool using a sensor, for example a spatial sensor 130, to output a three-dimensional representation of the current state of the ground surface. As with the previous implementation, the volume comparison module 820 accesses 855 the digital file describing the expected state of the site. Using the digital file and the representation of the current state to describe the amount of earth excavated from the hole, the volume comparison module 820 determines 860 a volume difference between the two representations describing the volume of earth within the tool. When comparing 865 the determined volume difference to a threshold difference, if the volume difference is less than a threshold difference, the volume check module 540 readjusts and maintains the leading edge of the tool beneath the ground surface to adjust the angle of the tool and reiterates 870 over the target tool path. Alternatively, if the volume difference is greater than a threshold difference, the topsoil identification module 910 distinguishes 875 between the layer of topsoil and the layer of subsoil. Further details regarding the topsoil identification module are described below in Section IV.G. Based on the identified layer of soil of the earth within the tool, the volume check module 540 empties 880 the earth from the volume tool at corresponding dump location.

In an additional implementation, the volume check module 540 records the output of a sensor, for example a linear encoder, a radial encoder, and a hydraulic pressure sensor, and determines the distance between the sensor and the tool. Using the determined distance, the current volume representation generator 810 generates a representation of the current state of the surface. The remaining steps are executed by the volume comparison module 820 and the topsoil identification module 910 as described above.

IV.F. Soil Layer Analysis

The topsoil identification module 910 is further configured to be able to access a set of properties describing the layer of topsoil and a set of soil composition properties describing the layer of subsoil, for example the density of the earth in the tool, the cohesion of the earth in the tool, the particle size of the earth in the tool, or the color of the particles of earth in the tool. The topsoil identification module 910, distinguishes topsoil excavated during a first set of target tool paths from subsoil excavated during a set of subsequent target tool path based on changes in the soil composition properties described above. After executing the set of instructions for the topsoil excavation routine, the topsoil identification module 910 determines that the entire layer of topsoil has been removed and transitions to executing a set of instructions for the subsoil excavation routine.

Topsoil and subsoil excavation routines may vary in a variety of ways, including but not limited to the speed or depth of digging for incumbent target tool paths, the location of the dump site, and so on.

When releasing earth from the tool, the volume check module 540 may release excavated earth from the topsoil layer at a top-soil specific dump pile and then automatically transition to release excavated earth from the subsoil layer at a sub-soil specific dump pile. The volume check module 540 may selectively release earth within tool at various dump piles based on various soil composition properties or ranges in soil composition properties and selectively retrieve earth from specific piles when backfilling sections of the hole. In another implementation, the volume check module 540 can maintain a single dump pile by releasing topsoil in a first direction and releasing subsoil in a second direction. When backfilling the hole, the volume check module 540 may retrieve earth from the dump pile based on the direction at which it was released.

IV.G. Updating the Predictive Model

The volume check module 540 may update the predictive excavation model based on data collected before, during, or after the completion of a target tool path to guide the movement of the excavation vehicle 115 within the site during any additional target tool paths. For example, the volume check module 540 can update the trained predictive model discussed above with data with collected during the completed target tool path and implement the updated predictive model to determine the horizontal distance that the tool must travel, at a known depth below the ground surface, to excavate the remaining amount of earth. The volume check module 540 may update the predictive model to define a relationship between the depths of the tool below the ground surface of the leading edge, the horizontal distance traversed by the tool, the amount of earth loaded into the tool, the soil composition within the site, and the tool width.

V. Soil Property Analysis

Figure 9:
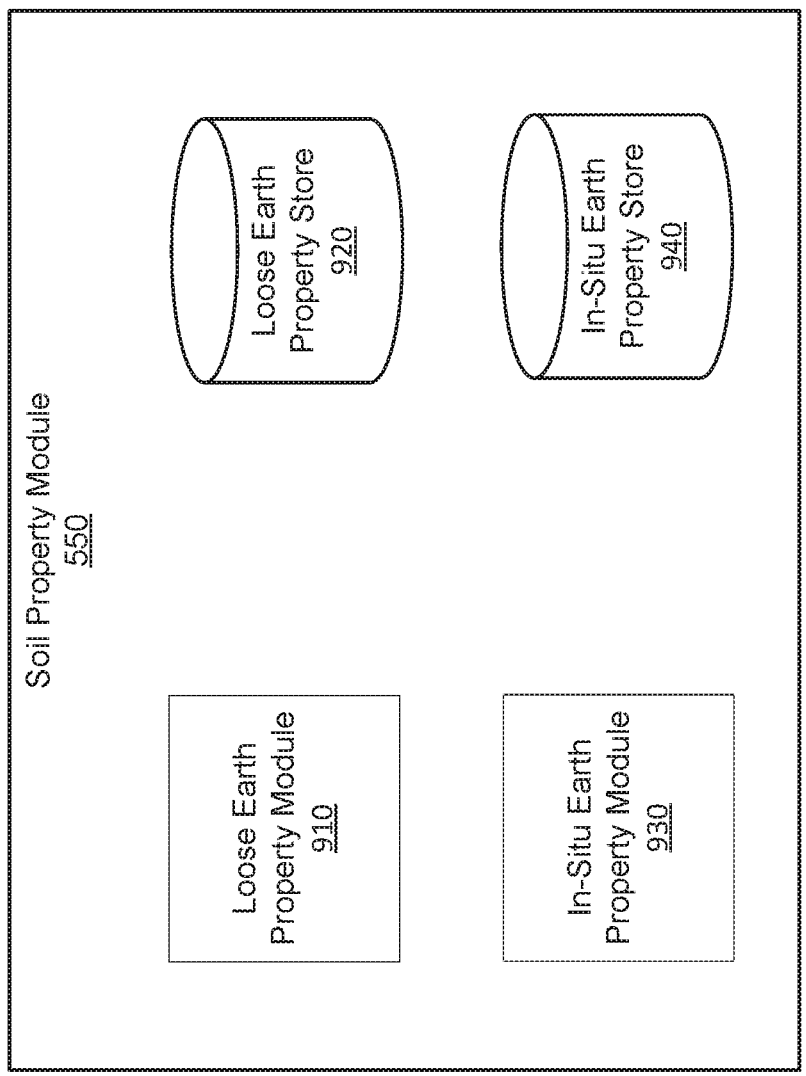
FIG. 9 is a diagram of the system architecture for the soil property module of an excavation vehicle, according to an embodiment.

FIG. 9 is a diagram of the system architecture for the soil property module 550 of an excavation vehicle 115, according to an embodiment. The soil property module 550 extrapolates earth composition properties from the movement of the tool, the hydraulic distribution of the engine system, optical scans, and other data collected by the excavation vehicle 115 during a target tool path and a subsequent volume check routine. The system architecture of the soil property module 550 comprises a topsoil identification module 910 (described above in Section IV.G), a loose earth property module 920, a loose earth property store 930, an in-site earth property module 930, and an in-site earth property store 940. In other embodiments, the soil property module 550 may include more or fewer modules. Functionality indicated as being performed by a particular module may be performed by other modules instead. Some of the modules of the soil property module 550 may be stored in the control logic module 500.

V.A. Loose Earth Properties

The loose earth property module 920 calculates earth properties of earth excavated from the hole, for example the density of the loose earth, and the loose earth property store 930 stores the calculated properties. In one implementation, the loose earth property module 920 uses the sensors to scan the tool during a check routine to calculate the particles size or range of particle sizes of the earth within the tool. Using the sensors, the loose earth property module 920 may implement various image recognition techniques including, but not limited to, template matching, object recognition, edge detection, or other computer vision techniques to identify distinct masses from the earth within the tool. The identified masses are correlated with known particle classifications, for example mud, sand, pebbles, small rocks, and larger rocks based on size, shape, and color of these distinct masses. Using the identified particles, the navigation module 510 may halt the navigation of the tool along the target tool path or prompt a human operator to manually move the tool along the target tool path. Alternatively, if the particle sizes exceed a maximum threshold, the earth removal module 520 switches to an alternate digging routine (e.g., a grading routine) at the end of the target tool path or in the middle of the target tool path. The controller 150 may also alternate to a grading routine in response to a high or low estimate of soil cohesion or an estimated maximum particle size lower than the tool depth during the grading routine.

V.B. In-Situ Earth Properties

The in-situ earth property module 940 calculates earth properties for earth within the hole prior to excavation, for example the density of the in-situ earth, and the in-situ earth property store 950 stores the calculated properties. In-situ earth describes earth within the site has not been excavated by the tool or earth is not yet within the tool. The sensors 170 record data across the hole or locally around the location of the target tool path prior to excavation to generate a first pre-load representation of the hole and repeat the process to generate a second pre-load representation of the hole for any subsequent target tool paths. The in-situ earth property module 940 can determine the difference between the first and second pre-load representations to calculate the volumetric change in the hole after the first target tool path. The in-situ earth property module 940 divides the weight of the earth in the tool, measuring using the sensor assembly 105, after the first target tool path to calculate the in-situ density of earth in the site.

The in-situ earth property module 940 may estimate the cohesion of excavated earth to be inversely proportional to a difference between the in-site earth density and the loose earth density. In another implementation, the in the friction (or adhesion) of in-situ earth based on a difference between the ground speed and wheel speed of the drive system 210 over a target tool path at a known orientation of the tool, position of the tool, and output torque of the engine system.

The in-situ earth property module 940 may implement similar methods and techniques to calculate texture, structure, consistency, and permeability of in-situ earth in the hole. Additionally, the in-situ earth property module 940 may reference a parametric soil type model to identify a type of soil using the in-site and loose earth properties of the earth within the site.

V.C. Wall Cutback Routines

In one implementation (not shown in FIG. 1-9), the preparation module 520 automatically modifies a wall cutback angle or a wall step size for the hole, for example as stored in the digital file or digital terrain model for the excavation routine, based on estimated composition of the earth removed from the hole during a digging routine. In particular, a requisite draft angle of a hole may be a function of one or more soil properties, for example soil type, density, particle size, and soil cohesion. As a result, the soil property module 550 may track soil properties during each target tool path within a digging routine, estimate various properties of in-situ and loose earth as described above, pass these soil properties into a lookup table or parametric model to calculate a requisite cutback angle for the current or subsequent target tool path, and adjust the target geometry of the hole based on requisite cutback angles calculated for each target tool path. For example, before beginning a digging routine, the preparation module 520 implements a conservative estimate of soil stability at various depths based on soil type data collected from the target tool paths, a soil report accessed from a previously excavated site, or soil data provided manually by a human operator and generates an initial target geometry of the hole with cutback angles suitable for the conservative soil stability estimate. The earth removal module 520, then, executes a sequence of target tool paths to form a hole according to this initial target geometry.

In some implementations, the controller 150 excavates earth and generates more refined estimates of the composition of soil at various depths of the site, the preparation module 520 calculates steeper cutback angles if the earth within the hole is determined to be more stable than originally projected and revises the remaining depth of the target hole geometry to reflect the steeper cutback angle. Alternatively, if the soil property module 550 determines that the earth is less stable than originally projected based on soil composition, the preparation module 520 can update the target geometry of the hole to reflect shallower cutback angles and removes earth from the existing walls of the hole to expand the footprint of the top hole to meet the final target geometry of the hole. Earth may be removed from the existing walls by scraping earth from the walls of the hole using the tool. As a result, by adjusting the target geometry of the hole to reflect the stability of excavated earth during the digging routine, the earth removal module 530 can maintain a stable hole while optimizing the total volume of earth to be excavated from the hole. The set of instructions describing a wall cutback routine also include an estimate of the time it will take to complete the excavation routine for a site. Routines including a greater number of cutbacks will generally result in longer time estimates, all else being equal.

The controller 150 may implement closed-loop techniques to cut sidewalls of the hole during or at the conclusion of a target tool path. For example, to cut a sidewall of a hole, the earth removal module 530 lowers the leading edge of the tool into the bottom corner of the hole, drives the leading edge of the tool relative to the surface of the sidewall to maintain an estimate of the tool depth, monitors the engine load and line pressure in the hydraulic system, and adjusts the elevation speed of the tool and the tool angle, as described above. In another implementation, the excavation vehicle 115 remains in one location within the hole, and the earth removal module 530 repeats the process for the same section of the sidewall until a target sidewall profile is achieved, and moves to the next section of the side wall to repeat the process until the estimated or measured amount of earth in the tool exceeds a minimum amount. At that time, the navigation module 510 navigates to the dump pile and releases the earth within the tool.

V.D. Backfill and Compaction Routines

The on-unit computer 120a may further include instruction sets to collect earth from the dump pile and backfill voids within the hole during backfill routines. For example, once a foundation wall or retaining wall is constructed within a hole previously dug by the excavation vehicle 115 may retrieve earth from the dump pile and dispense the earth between the exterior of the foundation wall and the wall of the hole around the foundation wall according to the digital file of the site.

After dumping earth into the void during one or a sequence of backfill routines, the controller 150 may execute a compaction routine to compact this backfilled earth. For example, after one or more bucket loads are emptied into the hole, the excavation vehicle 115 approaches the hole and the controller 150 raises the bucket, orients the bucket with the leading edge pointed downward, drives the bucket downward into the earth to compact this backfilled earth, and repeats this compaction routine until a sufficient level of compaction has been reached.

The controller 150 may implement closed-loop controls to control the entry speed of the leading edge of the tool as it makes contact with backfilled earth to achieve the target compact defined by the digital file or calculated by the preparation module 520 based on properties of the backfilled earth. Too little compaction of the earth results in the backfilled earth slumping, but excessive compaction results in the cracking of the adjacent foundation or retaining wall. Within these parameters, the preparation module 520 calculates a target compaction to yield less than 2" of slumping over a five-year period based on the density, cohesion, and particle size of the loose earth retrieved from the dump pile and the depth and breadth of the hole to be filled. The calculation of the target compaction may be done using a lookup table or a parametric model.

Additionally, the preparation module 520 may retrieve a total weight and a leading edge profile, describing the number and width of the teeth extending from the leading edge of the tool, and calculate an entry speed of the bucket and a number of compaction routines to achieve the target compaction level as a function of the density of the backfilled earth and the density of the compacted earth at the target compaction. The controller 150 may distribute the calculated number of compaction cycles evenly over backfilled earth according to the calculated entry speed. The controller 150 repeats the process for each of multiple backfill levels until the void is filled. The controller 150 may also implement any other process or tool, for example a vibrator plate compactor, to backfill the hole and compact the backfilled earth.

VI. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for analyzing an amount of earth in a tool, the method comprising:
   measuring, by a sensor mounted to an earth moving vehicle (EMV), a depth of a tool of the EMV beneath a ground surface and a distance that the tool was moved beneath the ground surface;
   executing, with a computer of the EMV, a set of instructions configured to cause the EMV to:
      determine a volume of earth within the tool based on the depth of the tool beneath the ground surface and the distance that the tool was moved beneath the ground surface; and
      adjust a position and an orientation of the tool relative to the ground surface based on the volume of earth within the tool.

2. The method of claim 1, wherein instructions for determining the volume of earth within the tool based on the depth of the tool beneath the ground surface and a distance that the tool was moved beneath the ground surface cause the EMV to:
   access a mathematical function trained to determine the volume of earth within the tool; and
   apply the mathematical function to determine the volume of earth within the tool, wherein the mathematical function integrates the depth of the tool beneath the ground surface over the distance that the tool was moved beneath the ground surface to determine the volume of earth within the tool.

3. The method of claim 1, wherein instructions for determining the volume of earth within the tool based on the depth of the tool beneath the ground surface and a distance that the tool was moved beneath the ground surface cause the EMV to:
   access a predictive model trained to predict the volume of earth within the tool based on a training dataset of labeled volumes of earth in the tool and sensor data describing positions and depths of the tool that contributed to each labeled volume of earth; and
   input the depth of the tool beneath the ground surface and the distance that the tool was moved beneath the ground surface into the predictive model to determine the volume of earth within the tool.

4. The method of claim 3, wherein the predictive model is further trained to predict the volume of earth within the tool based on one or more of:
   a type of the tool;
   a width of the tool; and
   a type of the EMV.

5. The method of claim 1, wherein the set of instructions further cause the EMV to:
- determine an available volume in the tool when empty based on geometric dimensions of the tool; and
- determine the volume of earth within the tool based on a comparison of the determined available volume in the tool when empty, the distance that the tool was moved beneath the ground surface, and an orientation of the tool beneath the ground surface.

6. The method of claim 5, wherein instructions further cause the EMV to:
- determine a force of earth acting on the tool as the tool moves over the distance at the depth beneath the ground surface;
- determine the orientation of the tool beneath the ground surface based on the force of earth acting on the tool; and
- determine the volume of earth within the tool based on the determined orientation of the tool beneath the ground surface and an amount of time that the tool has been fixed at the determined orientation.

7. The method of claim 5, wherein instructions further cause the EMV to:
- determine, by a sensor mounted to the tool, the orientation of the tool relative to a direction of gravity and an amount of time that the tool has been fixed at the orientation; and
- determine a volume of earth within the tool based on the determined orientation of the tool relative to the ground surface and the amount of time that the tool has been fixed at the determined orientation.

8. A non-transitory computer readable storage medium storing instructions for analyzing an amount of earth in a tool encoded thereon that, when executed by a processor, cause the processor to:
- measure, by a sensor mounted to an earth moving vehicle (EMV), a depth of a tool of the EMV beneath a ground surface and a distance that the tool was moved beneath the ground surface;
- determine a volume of earth within the tool based on the depth of the tool beneath the ground surface and the distance that the tool was moved beneath the ground surface; and
- adjust a position and an orientation of the tool relative to the ground surface based on the volume of earth within the tool.

9. The non-transitory computer readable medium of claim 8, wherein instructions for determining the volume of earth within the tool based on the depth of the tool beneath the ground surface and a distance that the tool was moved beneath the ground surface cause the processor to:
- access a mathematical function trained to determine the volume of earth within the tool; and
- apply the mathematical function to determine the volume of earth within the tool, wherein the mathematical function integrates the depth of the tool beneath the ground surface over the distance that the tool was moved beneath the ground surface to determine the volume of earth within the tool.

10. The non-transitory computer readable medium of claim 8, wherein instructions for determining the volume of earth within the tool based on the depth of the tool beneath the ground surface and a distance that the tool was moved beneath the ground surface cause the processor to:
- access a predictive model trained to predict the volume of earth within the tool based on a training dataset of labeled volumes of earth in the tool and sensor data describing positions and depths of the tool that contributed to each labeled volume of earth; and
- input the depth of the tool beneath the ground surface and the distance that the tool was moved beneath the ground surface into the predictive model to determine the volume of earth within the tool.

11. The non-transitory computer readable medium of claim 8, further comprising instructions that cause the processor to:
- determine an available volume in the tool when empty based on geometric dimensions of the tool; and
- determine the volume of earth within the tool based on a comparison of the determined available volume in the tool when empty, the distance that the tool was moved beneath the ground surface, and an orientation of the tool beneath the ground surface.

12. The non-transitory computer readable medium of claim 11, further comprising instructions that cause the processor to:
- determine a force of earth acting on the tool as the tool moves over the distance at the depth beneath the ground surface;
- determine the orientation of the tool beneath the ground surface based on the force of earth acting on the tool; and
- determine the volume of earth within the tool based on the determined orientation of the tool beneath the ground surface and an amount of time that the tool has been fixed at the determined orientation.

13. The non-transitory computer readable medium of claim 11, further comprising instructions that cause the processor to:
- determine, by a sensor mounted to the tool, the orientation of the tool relative to a direction of gravity and an amount of time that the tool has been fixed at the orientation; and
- determine a volume of earth within the tool based on the determined orientation of the tool relative to the ground surface and the amount of time that the tool has been fixed at the determined orientation.

14. A method for analyzing an amount of earth in a tool, the method comprising:
- accessing data recorded by a sensor mounted to an earth moving vehicle (EMV) representing a current state of a location, wherein the current state resulted from moving a volume of earth from the location using a tool of the EMV;
- executing, with a computer of the EMV, a set of instructions configured to cause the computer to:
  - determine a volume of earth within the tool based on a difference between the current state of the location with an initial state of the location prior to the movement of the volume of earth from the location; and
  - adjust a position and an orientation of the tool relative to a ground surface of the location based on the volume of earth within the tool.

15. The method of claim 14, wherein the current state of the location is a point cloud generated based on the data recorded by the sensor mounted to the EMV.

16. The method of claim 14, wherein the instructions further cause the EMV to:
- generate a digital map representing the initial state of the location using data recorded by the sensor before the volume of earth was moved from the location;

generate a digital map representing the current state of the location using the accessed data recorded by the sensor; and comparing the digital map representing the initial state of the location to the digital map representing the current state of the location to determine the volume of earth within the tool.

17. The method of claim 14, wherein the instructions for determining the volume of earth within the tool further cause the computer to:

access a representation of the initial state of the location, the representation of the initial state generated based on data collected by the sensor mounted to the EMV prior to the movement of earth from the location by the tool and comprising features in the location;

generate a representation of the current state of the location based on the data recorded by a sensor mounted to an earth moving vehicle, the representation of the current state of the location comprising features in the location; and align features of the representation of the initial state with features of the representation of the current state to determine the difference between the initial state and the current state of the location, wherein the determined difference represents a volume of earth moved from the location by the tool; and determine the volume of earth in the tool based on the volume of earth moved from the location by the tool.

18. The method of claim 14, wherein the instructions for determining the volume of earth within the tool further cause the computer to:

determine a pre-excavation volume of earth in the location representing the initial state of the location;

access a swell factor relating the pre-excavation volume of earth in the location to the volume of earth within the tool; and determine the volume of earth within the tool based on the pre-excavation volume of earth and the swell factor.

19. A non-transitory computer readable storage medium storing instructions for analyzing an amount of earth in a tool encoded thereon that, when executed by a processor, cause the processor to:

access data recorded by a sensor mounted to an earth moving vehicle (EMV) representing a current state of a location, wherein the current state resulted from moving a volume of earth from the location using a tool of the EMV;

determine a volume of earth within the tool based on a difference between the current state of the location with an initial state of the location prior to the movement of the volume of earth from the location; and adjust a position and an orientation of the tool relative to a ground surface of the location based on the volume of earth within the tool.

20. The non-transitory computer readable medium of claim 19, wherein the current state of the location is a point cloud generated based on the data recorded by the sensor mounted to the EMV.

21. The non-transitory computer readable medium of claim 19, further comprising instructions that cause the processor to:

generate a digital map representing the initial state of the location using data recorded by the sensor before the volume of earth was moved from the location;

generate a digital map representing the current state of the location using the accessed data recorded by the sensor; and comparing the digital map representing the initial state of the location to the digital map representing the current state of the location to determine the volume of earth within the tool.

22. The non-transitory computer readable medium of claim 19, wherein the instructions for determining the volume of earth within the tool further cause the processor to:

access a representation of the initial state of the location, the representation of the initial state generated based on data collected by the sensor mounted to the EMV prior to the movement of earth from the location by the tool and comprising features in the location;

generate a representation of the current state of the location based on the data recorded by a sensor mounted to an earth moving vehicle, the representation of the current state of the location comprising features in the location; and align features of the representation of the initial state with features of the representation of the current state to determine the difference between the initial state and the current state of the location, wherein the determined difference represents a volume of earth moved from the location by the tool; and determine the volume of earth of earth in the tool is the volume of earth moved from the location by the tool.

23. The non-transitory computer readable medium of claim 19, wherein the instructions for determining the volume of earth within the tool further cause the processor to:

determine a pre-excavation volume of earth in the location representing the initial state of the location;

access a swell factor relating the pre-excavation volume of earth in the location to the volume of earth within the tool; and determine the volume of earth within the tool based on the pre-excavation volume of earth and the swell factor.

\* \* \* \* \*